US011033336B2

(12) United States Patent
Bohl

(10) Patent No.: US 11,033,336 B2
(45) Date of Patent: *Jun. 15, 2021

(54) SYSTEMS AND METHODS FOR CONSTRUCTING A SYNTHETIC ANATOMICAL MODEL WITH PREDETERMINED ANATOMIC, BIOMECHANICAL, AND PHYSIOLOGICAL PROPERTIES

(71) Applicant: DIGNITY HEALTH, Phoenix, AZ (US)

(72) Inventor: Michael A. Bohl, Phoenix, AZ (US)

(73) Assignee: Dignity Health, San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/943,907

(22) Filed: Jul. 30, 2020

(65) Prior Publication Data

US 2020/0360090 A1 Nov. 19, 2020

Related U.S. Application Data

(63) Continuation of application No. 16/489,431, filed as application No. PCT/US2018/035223 on May 30, 2018, now Pat. No. 10,736,698.

(Continued)

(51) Int. Cl.
*A61B 34/10* (2016.01)
*G09B 23/30* (2006.01)

(Continued)

(52) U.S. Cl.
CPC .............. *A61B 34/10* (2016.02); *A61B 6/032* (2013.01); *A61B 6/505* (2013.01); *B29C 64/393* (2017.08);

(Continued)

(58) Field of Classification Search
CPC ... B33Y 80/00; A61B 34/10; A61B 2034/105; A61F 2002/30948; G09B 23/30; G09B 23/28; G16H 50/50
See application file for complete search history.

(56) References Cited

U.S. PATENT DOCUMENTS 5,741,215 A 4/1998 D'Urso
2011/0118527 A1 5/2011 Giesel et al.

(Continued)

FOREIGN PATENT DOCUMENTS

WO 2018/222779 A1 12/2018

OTHER PUBLICATIONS

Ploch, et al. "Using 3D Printing to Create Personalized Brain Models for Neurosurgical Training and Preoperative Planning." World Neurosurgery [online], 2016, vol. 90 pp. 668-674. See Entire Document, especially Fig. 4; p. 568, col. 1, para 3; p. 668, col. 2, para 1; p. 669, col. 1, par 3; p. 669, col. 2, para 2; p. 670, col. 2 para 2.

(Continued)

*Primary Examiner* — Jerry-Daryl Fletcher
(74) *Attorney, Agent, or Firm* — Law Offices of Damon L. Boyd, PLLC

(57) ABSTRACT

A computing device and a three-dimensional printer are disclosed. Data associated with reference anatomical properties is accessed by the computing device to generate a set of 3D printing files. The 3D printing files are compiled using the computing device to generate a printing model defining an anatomic orientation corresponding to the reference anatomical properties. Printing parameters and materials for the printing model are configured referencing experimentally derived datasets that define predetermined settings for the printing parameters and materials that are suitable for constructing a synthetic anatomical model with properties (Continued)

250
272
17.6° related to the reference anatomical properties. A synthetic model is printed using the printing parameters and materials as configured. The printing parameters and materials may be modified as desired subsequent to biomechanical testing of the model. Additional synthetic anatomical components may be added to or included with the model during post-processing, or before or during formation of the model.

18 Claims, 29 Drawing Sheets

Related U.S. Application Data

(60) Provisional application No. 62/512,243, filed on May 30, 2017, provisional application No. 62/518,653, filed on Jun. 13, 2017, provisional application No. 62/589,756, filed on Nov. 22, 2017, provisional application No. 62/589,788, filed on Nov. 22, 2017, provisional application No. 62/589,733, filed on Nov. 22, 2017, provisional application No. 62/589,768, filed on Nov. 22, 2017, provisional application No. 62/589,780, filed on Nov. 22, 2017, provisional application No. 62/591,241, filed on Nov. 28, 2017.

(51) Int. Cl.

| | |
|---|---|
| ***G16H 50/50*** | (2018.01) |
| ***A61B 6/03*** | (2006.01) |
| ***A61B 6/00*** | (2006.01) |
| ***B33Y 50/02*** | (2015.01) |
| ***B29C 64/393*** | (2017.01) |
| ***B33Y 10/00*** | (2015.01) |
| ***G16H 30/40*** | (2018.01) |
| ***B33Y 80/00*** | (2015.01) |
| *B29L 31/00* | (2006.01) |

(52) U.S. Cl.

CPC ............... *B33Y 10/00* (2014.12); *B33Y 50/02* (2014.12); *B33Y 80/00* (2014.12); *G09B 23/30* (2013.01); *G09B 23/303* (2013.01); *G16H 30/40* (2018.01); *G16H 50/50* (2018.01); *A61B 2034/104* (2016.02); *A61B 2034/105* (2016.02); *B29L 2031/7532* (2013.01)

(56) References Cited

U.S. PATENT DOCUMENTS

| | | | | |
|---|---|---|---|---|
| 2012/0121660 | A1 | 5/2012 | Akella et al. | |
| 2012/0290976 | A1 | 11/2012 | Lahm et al. | |
| 2013/0085736 | A1 | 4/2013 | Reihsen et al. | |
| 2015/0250934 | A1 | 9/2015 | Sugimoto et al. | |
| 2017/0014169 | A1 | 1/2017 | Dean et al. | |
| 2020/0062969 | A1 * | 2/2020 | Chasser | C09D 175/06 |

OTHER PUBLICATIONS

European Application 18809330.6 Extended European Search Report dated Dec. 16, 2019.

Reply to Extended European Search Report dated Dec. 16, 2019 filed Jul. 10, 2020.

Non-Final Office Action dated Mar. 13, 2020 for U.S. Appl. No. 16/489,431.

Proposed Amendment provided to Examiner Jun. 5, 2020 for U.S. Appl. No. 16/489,431 for Examiner Interview.

Examiner Interview Summary dated Jun. 10, 2020 for U.S. Appl. No. 16/489,431.

Reply to Non-Final Office Action dated Mar. 13, 2020 for U.S. Appl. No. 16/489,431, filed Jun. 11, 2020.

Notice of Allowance dated Jun. 30, 2020 for U.S. Appl. No. 16/489,431.

Issue Fee Payment dated Jul. 1, 2020 for U.S. Appl. No. 16/489,431.

PCT Application No. PCT/US18/35223 filed May 30, 2018.

PCT Request for PCT Application No. PCT/US18/35223 filed May 30, 2018.

Notice of International Search Report for PCT Application No. PCT/US18/35223 dated Sep. 17, 2018.

International Search Report for PCT Application No. PCT/US18/35223 dated Sep. 17, 2018.

International Search Report Search Strategy for PCT Application No. PCT/US18/35223 dated Sep. 17, 2018.

Written Opinion for PCT Application No. PCT/US18/35223 dated Sep. 17, 2018.

Notice of Publication for PCT Application No. PCT/US18/35223 dated Dec. 6, 2018.

Dec. 1, 2020 Canadian Amendment/Remarks After Examiner's Report in Response to the Official Action dated Oct. 13, 2020.

Canadian Intellectual Property Office Notice of Requisition by the Examiner in Accordance with Subsection 86(2) of the Patent Rules dated Oct. 13, 2020.

* cited by examiner 640
642

SYSTEMS AND METHODS FOR CONSTRUCTING A SYNTHETIC ANATOMICAL MODEL WITH PREDETERMINED ANATOMIC, BIOMECHANICAL, AND PHYSIOLOGICAL PROPERTIES

CROSS REFERENCE TO RELATED APPLICATIONS

This Patent Application is a continuation-in-part of and claims priority under 35 U.S.C. § 120 to U.S. Pat. No. 10,736,698, entitled "SYSTEMS AND METHODS FOR CONSTRUCTING A SYNTHETIC ANATOMICAL MODEL WITH PREDETERMINED ANATOMIC, BIOMECHANICAL, AND PHYSIOLOGICAL PROPERTIES," filed Aug. 28, 2019, which is related to and claims priority under 35 U.S.C. § 371(c) to the national stage entry application claiming priority under 35 U.S.C. § 371(c) to PCT/US2018/035233, entitled "SYSTEMS AND METHODS FOR CONSTRUCTING A SYNTHETIC ANATOMICAL MODEL WITH PREDETERMINED ANATOMIC, BIOMECHANICAL, AND PHYSIOLOGICAL PROPERTIES," filed May 30, 2018, which is related to and claims priority under 35 U.S.C. § 119(e) to U.S. Provisional Patent Application No. 62/512,243, entitled "METHOD FOR CONSTRUCTING A SYNTHETIC SPINE MODEL WITH HIGH ANATOMIC AND BIOMECHANICAL FIDELITY TO A CADAVERIC SPINE MODEL," filed May 30, 2017; U.S. Provisional Patent Application No. 62/518,653, entitled "METHOD FOR CONSTRUCTING A SYNTHETIC SPINE MODEL WITH HIGH ANATOMIC AND BIOMECHANICAL FIDELITY TO A CADAVERIC SPINE MODEL," filed Jun. 13, 2017; U.S. Provisional Patent Application No. 62/591,241, entitled "SYSTEM AND METHOD FOR CONSTRUCTING A SYNTHETIC SPINE MODEL WITH ANATOMIC, BIOMECHANICAL, AND PHYSIOLOGICAL FIDELITY TO A SPINE MODEL," filed Nov. 28, 2017; U.S. Provisional Patent Application No. 62/589,756, entitled "SYSTEM AND METHOD FOR 3-D PRINTED OSTEOTOMY MODELS," filed Nov. 22, 2017; U.S. Provisional Patent Application No. 62/589,788, entitled "SYSTEM AND METHOD FOR 3-D PRINTED MODELS," filed Nov. 22, 2017; U.S. Provisional Patent Application No. 62/589,733, entitled "Systems and Methods for Fluoroscopic analysis of a synthetic spine model made of variable 3D-printed materials," filed Nov. 22, 2017; U.S. Provisional Patent Application No. 62/589,768, entitled "SYSTEM AND METHOD FOR 3-D PRINTED MODELS FOR PEDICLE SCREW INSERTION," filed Nov. 22, 2017; and U.S. Provisional Patent Application No. 62/589,780, entitled "SYSTEM AND METHOD FOR 3-D PRINTED MODELS," filed Nov. 22, 2017; all of which are fully incorporated by reference herein for all purposes.

FIELD

The present disclosure generally relates to systems and methods for creating synthetic anatomical models. More specifically, the present application describes systems and methods for configuring an apparatus comprising a three-dimensional printer and computing device to construct a base synthetic anatomical model with specific predefined anatomic, biomechanical, and physiological properties, which may be supplemented with additional synthetic anatomical components before, during, or post-processing.

BACKGROUND

Synthetic spine models and other anatomical models are critical to surgical education, patient education, the development and testing of new surgical treatment strategies, the development and testing of new devices for use in the treatment of spinal disorders, and as a research platform in spine biomechanical studies. Cadaveric spines are currently used as a standard educational and research platform for most of the above purposes. Cadaveric spines come with many limitations, however, that make their utility in surgical education, biomechanical research, and/or with new device testing platform highly limited.

Disadvantages of cadaveric spine models include their expense, difficulty in acquisition (via donors at the time of death), human tissue handling restraints and institutional requirements for cadaveric testing, risk to laboratory personnel when handling human tissue, inability (or very high difficulty) in obtaining models of specific pathologies, and high variability in biomechanical performance between specimens (thought to be due to variations in preservation technique, age of cadaveric specimen, and bone and soft tissue quality of donor at the time of death) which results in wider result variability during biomechanical testing. This wider result variability must be overcome by using larger numbers of cadavers during testing, further increasing the cost, tissue handling requirements, and subsequent risks.

It is with these observations in mind, among others, that various aspects of the present disclosure were conceived and developed.

BRIEF DESCRIPTION OF THE DRAWINGS

Corresponding reference characters indicate corresponding elements among the view of the drawings. The headings used in the figures do not limit the scope of the claims.

DETAILED DESCRIPTION

Figure 1:
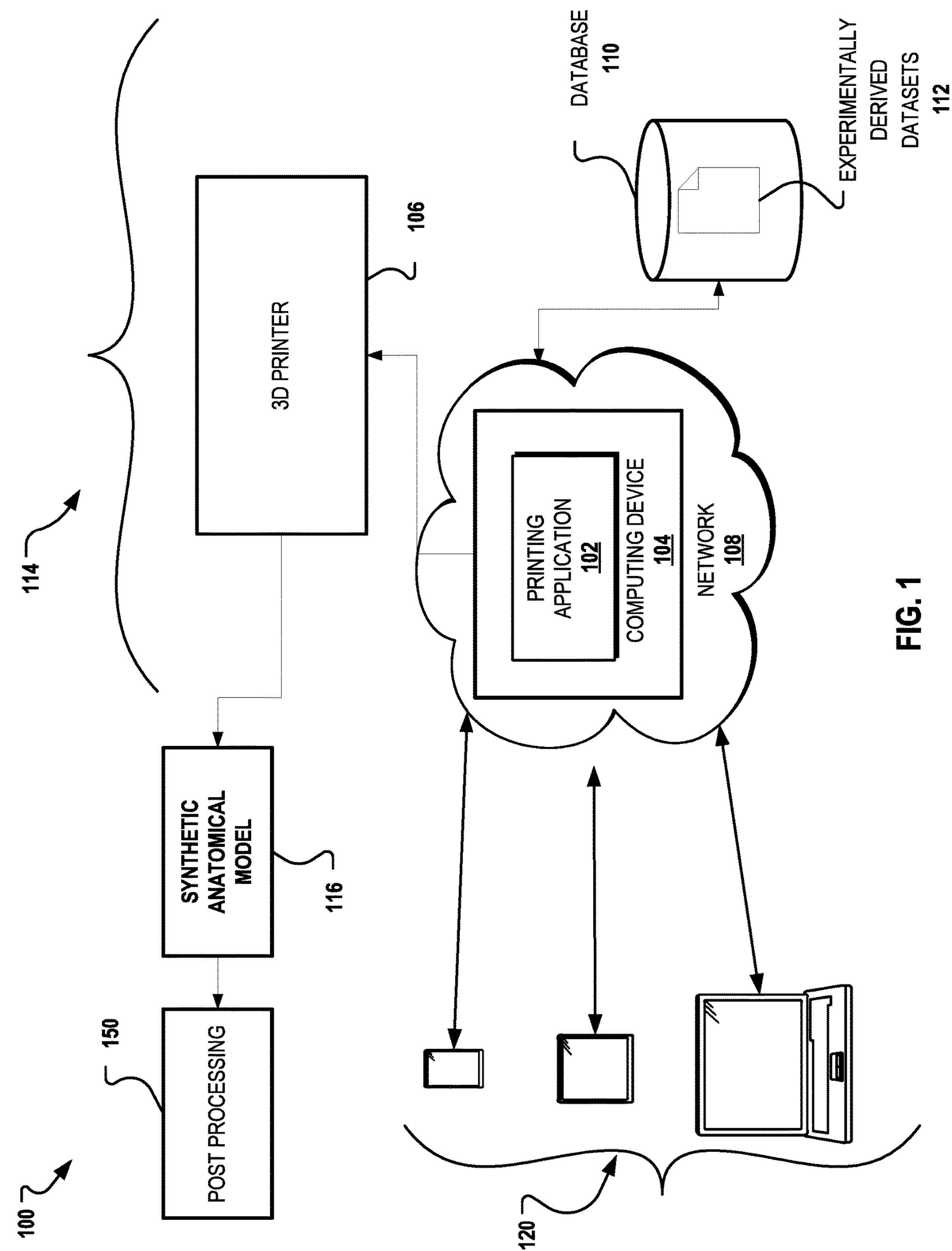
FIG. 1 is a simplified block diagram illustrating a system for configuring an apparatus comprising a three-dimensional printer and computing device for constructing a synthetic anatomical model with specific predefined anatomic, biomechanical, and physiological properties.

An ideal platform for performing surgical education (e.g., for medical students, physicians, medical-industry personnel, patients, etc.), biomechanical testing, and new medical device testing may have at least the following features: comprised of synthetic materials with indefinite or very long shelf life; very high fidelity to human tissue in terms of gross anatomy, radiographic anatomy, biomechanical performance of synthetic bone material, and biomechanical performance of synthetic soft tissue materials; ability to construct this platform to mimic any normal or pathological state of anatomy; and ability to include in the platform certain features that allow the platform to mimic physiological functions including but not limited to bleeding, electrical conductivity, leakage of spinal fluid, and monitoring of pressures within certain areas of the model.

Accordingly, in view of the aforementioned and other observations, the present disclosure relates to an inventive system and methods for construction of anatomical models which may include synthetic spine models and/or other synthetic anatomical components. Comprehensive research and testing methods were conducted to generate experimentally derived datasets that have been found to be advantageous towards configuring a computing device and/or a three-dimensional (3D) printer for forming customized synthetic anatomical base models, such as a synthetic 3D-printed vertebra base model or other spinal segment that exhibits high anatomical, physiological, and biomechanical fidelity relative to a cadaveric vertebra or other bone tissue, or otherwise exhibits characteristics that conform with specific predetermined properties. Specifically, in one embodiment, image data may be extracted or generated from a plurality of sample (living or cadaveric) vertebral segments. Each of the sample vertebral segments may exhibit or include various different biomechanical, anatomical, and/or physiological properties such that the integrated image data is as comprehensive as desired; i.e., covers a suitable range of possible spinal segment properties. The integrated image data of the sample vertebral segments may then be compiled into one or more 3D printing files, and 3D models of the sample vertebral segments may be printed. The 3D models of the sample vertebral segments may then be subjected to various biomechanical tests as described herein to generate experimentally derived datasets defining relationships between properties associated with the sample vertebral models and materials and printing parameters for a 3D printer or additive manufacturing device. In other words, the experimentally derived datasets define or are otherwise informative as to the particular configuration of suitable materials and printing parameters unique for subsequently generating (by 3D printing or additive manufacturing) synthetic spine models or other anatomical components with certain properties corresponding to various examples of the sample vertebral segments (having different conditions, anatomical orientations, etc.).

The experimentally derived datasets may then be leveraged to construct a synthetic spinal segment model or other anatomical model with desired properties of any of the sample models (or properties from other sample information). For example, to generate a synthetic spinal model with an anatomical orientation similar or identical to a particular form of scoliosis, an experimentally derived dataset may be leveraged that has been previously generated from a sample cadaver model. These experimentally derived datasets can inform certain aspects of the 3D-printing process, including but not limited to the material used, the shell thickness, or the in-fill density, to generate a model with certain bony biomechanical properties. Similarly, an image dataset of a patient or cadaver with a certain type of scoliosis can be converted to a 3D file for modeling of that specific scoliotic anatomy. Print parameters, disc heights, facet joint modifications, and/or other 3D file or 3D printer modifications can then be employed to create a model with very high anatomical and biomechanical fidelity to a natural (.e.g., human or otherwise) spine with the same scoliotic curve. In other words, printing parameters and materials for a given 3D printing file may be configured or otherwise modified according to the experimentally derived datasets to construct a synthetic spinal segment with an anatomic orientation exhibiting the same or similar form of scoliosis. Accordingly, leveraging the experimentally derived datasets accommodates the 3D printing of a synthetic spine or other anatomical model that exhibits a set of desired or predetermined anatomical, biomechanical, and physiological characteristics.

In some embodiments, leveraging similar testing methods or other research as described, other anatomical components may be constructed and may include synthetic blood vessels, a synthetic thecal sac, synthetic muscle, and synthetic periosteum, and other synthetic mimics of anatomical components in addition to the 3D printed synthetic model, as further described herein. Referring to the drawings, one embodiment of a system for configuring an apparatus comprising a three-dimensional printer and computing device to construct a synthetic anatomical model with specific predefined anatomic, biomechanical, and physiological properties is illustrated and generally indicated as 100 in FIGS. 1-27.

Referring to FIG. 1, a non-limiting exemplary system 100 for construction of a synthetic anatomical model (such as a synthetic spinal segment) is shown. The system 100 may generally include a printing application 102 executed by a computing device 104, and a 3D printer 106 in operable communication with the computing device 104 (by wired connection or wirelessly connected) via a network 108. The printing application 102 and the computing device 104 may be configured to issue commands to the 3D printer 106 for constructing a synthetic spine segment or other anatomical model with predetermined properties, as described herein, among other features.

The computing device 104 may include one or more of a server, controller, a personal computer, terminal, workstation, laptop, mobile device, tablet, mainframe, or other such computing device configured by the application 102 or otherwise to implement functionality associated with 3D printing or additive manufacturing described herein. The printing application 102 may include or otherwise have access to functionality associated with one or more 3D imaging and/or printing software packages, specially configured or otherwise, and may include, e.g., Blender, Cura, OpenSCAD, Slic3r, 3D Slash, Design Spark Mechanical, Mimics, Simplify3D, and the like. The printing application 102 may be configured to convert images (high-resolution or otherwise) into a 3D modeling file, extract features of the images associated with desired anatomical components, and convert the features to .stl format or other printing file format as printing instructions. In addition, the printing application 102 may be further configured to transmit the instructions from the computing device 104 to the 3D printer 106 to print a synthetic model as described herein. Aspects of the computing system 100 and/or the printing application 102 may be provided using platform as a service (PaaS), and/or software as a service (SaaS) using e.g., Amazon Web Services, or other distributed or decentralized systems. The network 108 may include the Internet, an intranet, a virtual private network (VPN), a local area network (LAN), a wide area network (LAN), a peer-to-peer network, a cloud, and the like. In some embodiments, a cloud (not shown) may be implemented to execute one or more components of the computing system 100.

As indicated, the computing device 104 may be in operable connection with or may otherwise have access to a database 110. The database 110 may store experimentally derived datasets 112 and other associated information as described herein. Data from the datasets 112 stored in the database 110 may accessed by the application 102 and computing device 104 in real time or otherwise as desired, and may be updated as additional experimentally derived datasets 112 are generated or modified using the methods described herein.

As further indicated, the computing device 104, the printing application 102, the 3D printer 106, and the database 110 (including the experimentally derived datasets 112), may collectively define an apparatus 114. Configuring the apparatus 114 as described herein accommodates the construction of a synthetic anatomical model 116 with any number of specific predetermined anatomic, biomechanical, and physiological properties. In some embodiments, the synthetic anatomical model 116 may define a base synthetic anatomical model, which may be supplemented with additional synthetic components before, during, or subsequent to a post processing step 150 as further described herein.

In addition, at least some features of the printing application 102 may be made available to a plurality of user devices 120 in communication with the computing device 104 via the network 108. The plurality of user devices 120 may include, without limitation, at least one of a controller, a personal computer, terminal, workstation, portable computer, laptop, mobile device, tablet, phone, pager, or multimedia console. Any one of the plurality of user devices 120 may be implemented to e.g., submit information to the computing device 104 for modifying or supplementing the database 110, requesting a particular synthetic anatomical model, and the like.

Figure 2A:
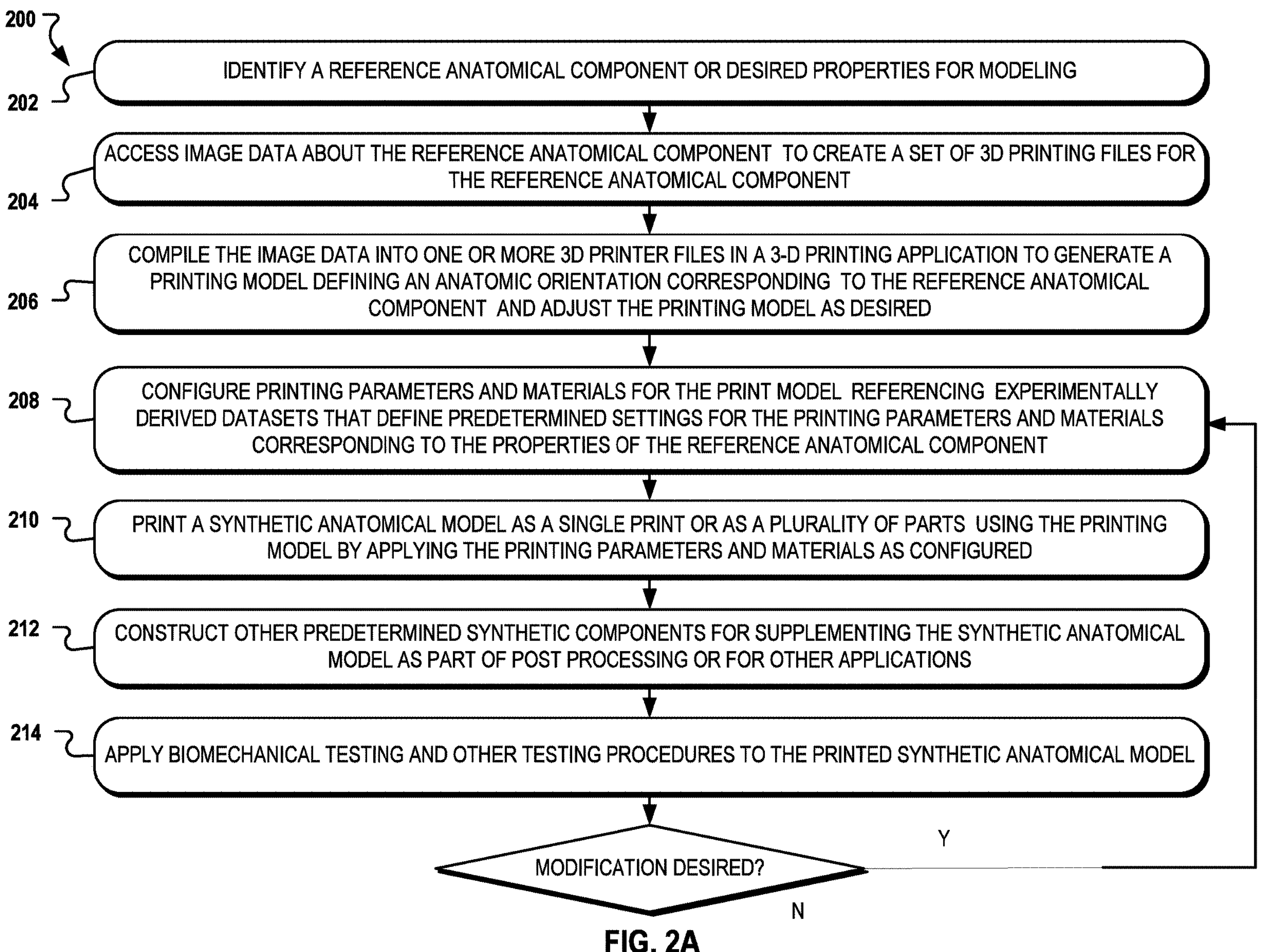
FIG. 2A is an exemplary process flow for utilizing the system of FIG. 1 to construct a synthetic anatomical model with specific predefined anatomic, biomechanical, and physiological properties.

Referring to FIG. 2A, with continuing reference to FIG. 1, a process flow 200 is shown for implementing the system 100 to construct the synthetic anatomical model 116 with specific predetermined anatomic, biomechanical, and physiological properties as desired leveraging the experimentally derived datasets 112. As shown in block 202, a reference anatomical component, such as a spinal segment, pelvic bone, temporal bone, or desired anatomical properties may first be selected, accessed, or identified. The reference anatomical component and/or properties may be selected from any number of data sources and may be associated with or represent any number of applications. For example, the reference anatomical component may include or may be representative of a reference spinal segment 250 (shown in FIG. 2B) of a particular patient that is scheduled for a spinal fixation procedure and application of a spinal fixation construct. In this example, the reference spinal segment 250 of the patient may include various particular anatomical, physiological, and biomechanical properties, and it may be desirable to generate the synthetic anatomical model 116 with properties similar to the reference spinal segment 250 of the patient in order to mimic or replicate the scheduled spinal fixation procedure by conducting one or more trial spinal fixation procedures to using one or more of the synthetic anatomical model 116 (modeled to mimic the reference spinal segment 250), in order to, e.g., provide the surgeon with surgical preparation time and training, and to proactively identify possible failure points of the natural reference spinal segment 250. Such preparation time and the ability to identify possible failure points can dramatically increase the probability of a successful procedure and generally increase confidence with the surgeon.

As another example, the reference spinal segment 250 or desired properties may be selected based on a particular training application desired for spinal surgeons. Specifically, the synthetic anatomical model 116 may be printed to help surgical trainees understand certain aspects of surgical anatomy, or to better perform certain surgical skills and techniques. In this manner, the synthetic anatomical model 116 may be capable of replicating the physical properties of cadaveric spines for the purposes of both resident education and biomechanical testing. This assists residents to learn complex spinal procedures through hands-on surgical manipulation of a 3D-printed spine replica that closely mimics the physical properties of the human vertebral column. As demonstrated by these examples, a reference spinal segment or desired anatomical properties may be selected from a cadaver, a living human or other animal/mammal (e.g., companion animal for veterinary applications), or the properties may be individually selected, e.g., it may be desired to print the synthetic anatomical model 116 with specific properties (e.g., a particular bone density) that do not necessarily conform to a specific cadaver or living animal. In some embodiments, the anatomical properties may be derived from non-human animals, such that the reference properties or reference anatomical components and the subsequently generated synthetic model may be useful for veterinary applications; e.g., modeling portions of a canine's spine. The user may decide what information is relevant to generate the desired synthetic anatomical model 116, such as a component that contains vascular anatomy, or artificial neural elements capable of conducting electricity, or any standard healthy anatomy or any number of patient-specific disease states, with, e.g., anatomical and biomechanical fidelity to that healthy or diseased-state. Specific examples of properties that it may be desired to replicate (and may ultimately be replicated as described herein) with the synthetic anatomical model 116 may include range of motion or flexibility, bone mineral density, anatomical shapes, textures, and dimensions, blood loss through bone, bleeding from direct vessel injury, monitoring of electrical signals through synthetic neural elements, monitoring of pressure in particular parts of the model such as the thecal sac to provide feedback on potential for neural element injury during a particular surgical maneuver, and radiographic feedback from the model under standard radiographic image processes such as fluoroscopy or computed tomography.

Referring to block 204 in FIG. 2A, in some embodiments, image data (not shown) associated with the reference anatomical component (e.g., the reference spinal segment 250) or the desired synthetic anatomical model 116 and/or spinal segment properties may be generated or otherwise accessed by the printing application 102 and/or the computing device 104 in preparation for 3D printing or additive manufacturing (which may ultimately be used to generate a 3D printable model for the synthetic anatomical model 116). In some embodiments, the image data may be generated using a computer-aided design (CAD) package (separately implemented or integrated within the printing application 102), and the generated image data may include one or more .STL files associated with stereolithographic CAD software (accessed or integrated with the printing application 102). The image data may also include DICOM® data defining a voxel-based morphometry of e.g., the reference spinal segment 250, pixel-based imaging of the reference spinal segment 250, and the like, which may be segmented or sliced. In some non-limiting embodiments, the user may access the image data through a visualization tool such as a magnetic resonance image ("MRI"), a computed topography ("CT"), an X-ray, an ultrasound, or any other digital visualization method applied to e.g., the reference spinal segment 250. In some embodiments, the image data may be generated using a 3D scanner or general photogrammetry software applied to e.g., the reference spinal segment 250. In some embodiments, the image data may be provided directly to the computing device 104 by tracking or scanning an image of e.g., the reference spinal segment 250 in real time, or by downloading a digital image associated with the reference spinal segment 250 into memory accessible to the computing device 104. The image data generated using any of the aforementioned scanning methods defines sequential digital layers associated with the shape and appearance of the reference spinal segment 250 or other reference anatomical component, which subsequently accommodates the creation of a 3D digital model (layer by layer) based on such image data, as further described herein.

In other non-limiting embodiments, no digital visualization method may be needed. To illustrate, the user may decide to compile a digital image from artificially generated data representative of certain predetermined anatomical properties desired by the user. For example, pre-generated 3D models of spinal segments, or other data, may be used on their own or combined with a digital visualization method. In addition, the image data can be compiled from multiple models of spinal segments from multiple patients, or one patient over different time periods. Moreover, it should be considered that the method may be used to generate any component of a human or non-human body. For example, it is also contemplated that this method may have use in the veterinary field as well.

Referring to block 206, the components of the image data may be compiled with, fed to, or otherwise accessed by the printing application 102 to generate one or more 3D printing files (or additive manufacturing files) defining a 3D model of the reference anatomical component, such as the reference spinal segment 250. In one embodiment, a command hierarchy of the printing application 102 may be used. For example, a user may select "File", then "Export" and then choose the ".stl" file format to convert the image data to one or more STL (stereolithography) files. This may also be achieved automatically by functionality of the printing application 102 designed to execute hierarchy commands. In other words, the printing application 102 may be configured to generate one or more 3D printing files, such as .STL files, based on the image data. The 3D printing files define a 3D printing model of e.g., the reference spinal segment 250.

In other embodiments, the printing application 102 may further be configured to generate other types of 3D printing files representative of a printing model of the reference spinal segment. For example, one or more additive manufacturing files (AMF)s may be generated defining a 3D printing model of the reference spinal segment that may be applied for additive manufacturing applications. Printing files associated with fused deposit modeling (FDM) may also similarly be generated and utilized.

In some embodiments, once the image data is compiled into one or more 3D printing files, data associated with the 3D printing files may be processed or examined for possible errors or adjustments and may be repaired as desired. For example, STL files may generally include abnormalities or errors in the form of holes, incorrect orientation of image features, and the like. At this stage, a user may interact with the printing application 102, or the application 102 may be programmed with functionality to change the dimensions of the 3D printing model to e.g., adjust orientation of features of the 3D printing model, fill in gaps or holes or otherwise adjust such features, separate inadvertently fused components of the 3D printing model to more closely model the reference spinal segment 250, and the like. The user may also modify the 3D printing model such that the model ultimately printed has either open or fused facet joints. In some embodiments, subsequent to any adjustments to the 3D printing model applied at this stage, the 3D printing files may be processed to convert the files into digital layers with instructions tailored specifically for specific 3D printers or additive manufacturing components.

In addition, a user may select a region of interest of the 3D printing model; for instance, a region representing a lamina of the reference spinal segment 250, and alter its default value, or values defined by the default 3D model as desired. The computing device 104 may further continuously compare a selected pixel or voxer with its neighboring pixels or voxers to determine their location and characteristics for matching, and may be configured with (via the printing application 102 or otherwise) with tools to morph or change parameters of the 3D printing model such that they are suitable for the user's purpose. In one non-limiting embodiment, the desired shape and construction of the synthetic anatomical model 116 can be simulated with just the user's judgement alone. Alternatively, the user may generate the 3D printing model based on a reference body, individual calculations, reference data, or with a software algorithm that can identify and create parameters to the user's needs. Such an algorithm may be implemented in other steps of the disclosed method as well, and the computer software can determine or calculate part of what the default 3D model should look like.

Referring to block 208, printing parameters and materials associated with the 3D printing model may be configured, referencing the experimentally derived datasets 112, so that the synthetic anatomical model 116 may ultimately be constructed with properties that simulate or resemble the properties of the reference anatomical component, such as the reference spinal segment 250 of block 202. The experimentally derived datasets 112 may include intelligence about specific configurations or selections of materials and print parameters suitable for constructing the synthetic anatomical model 116 with the desired properties of the reference spinal segment 250. Print parameters may include, e.g., a number of print shells, in-fill percentage, filament material, extruder temperature, print orientation, and in-fill pattern, among others. Possible materials may include Acrylonitrile butadiene styrene (ABS), a plastic polymer; Nylon; Polylactic Acid (PLA); or other 3D printing filaments such as Polyethylene terephthalate (PET); thermoplastic elastomer (TPE); thermoplastic polyurethane (TPU); high impact polystyrene (HIPS); polyvinyl alcohol (PVA); carbon fiber, polycarbonate; wood; metals; or combinations thereof, or any other different types of known printer filaments suitable for replicating aspects of the reference spinal segment 250 or other reference anatomical component or predefined anatomical properties.

To illustrate, defects in the spine, such as osteopenia, may result in pockets of low bone density in the subject's spinal segment. Accordingly, it may be desired to build the synthetic anatomical model 116 with pockets of low bone density along predetermined areas of the model. Referencing the experimentally derived datasets 112, the print parameters and the materials may be configured based on the experimentally derived datasets 112 to construct the synthetic anatomical model 116 to have a T-score of −1 or −2.5, or indeed whatever density is desired. In this way, a user may practice surgical techniques related to osteopenia on the synthetic anatomical model 116 or use it as surgical prosthetic. In one non-limiting embodiment, one or more default print parameters can be suggested by the printing application 102 and then this default can be adjusted by the user to their preference such that it matches the desired dimensions, or properties of the patient or the final design. As described herein, this may be accomplished by altering the print parameters and materials selection for the print; these alterations including, but not limited to shape, porosity, composition, structure, in whole or part of the component.

Referring to block 210, once the 3D printing model has been sufficiently adjusted as desired in block 206, and the print parameters and materials have been configured in block 208, the printing application 102 may generate a set of executable printing instructions (not shown) compatible with the 3D printer 106 or other printing or additive manufacturing device. The executable printing instructions may define the 3D printing model and instruct the 3D printer 106 to utilize a particular configuration of print parameters and materials settings and selections for printing the synthetic anatomical model 116.

The synthetic anatomical model 116 may then be printed with the predetermined physiological, anatomical, and biomechanical properties previously determined by configuring the materials and printing parameters described. Any number of different variations of the synthetic anatomical model 116 may be printed (by way of the executable printing instructions or otherwise) by leveraging the experimentally derived datasets 112 to print the model to customized specifications as desired for different applications. In one non-limiting embodiment, the disclosed method of FIG. 2A may service to replace or amend the use of cadaveric models in biomechanical testing. Unlike cadaveric models, the method of the present inventive concept creates the synthetic anatomical model 116 with components that are completely customizable, thereby replacing the need to implement cadavers for biomechanical testing. The customizable synthetic anatomical model 116 may correspond to the reference spinal segment and the 3D printable model generated from the image data, or otherwise.

Figure 2C:
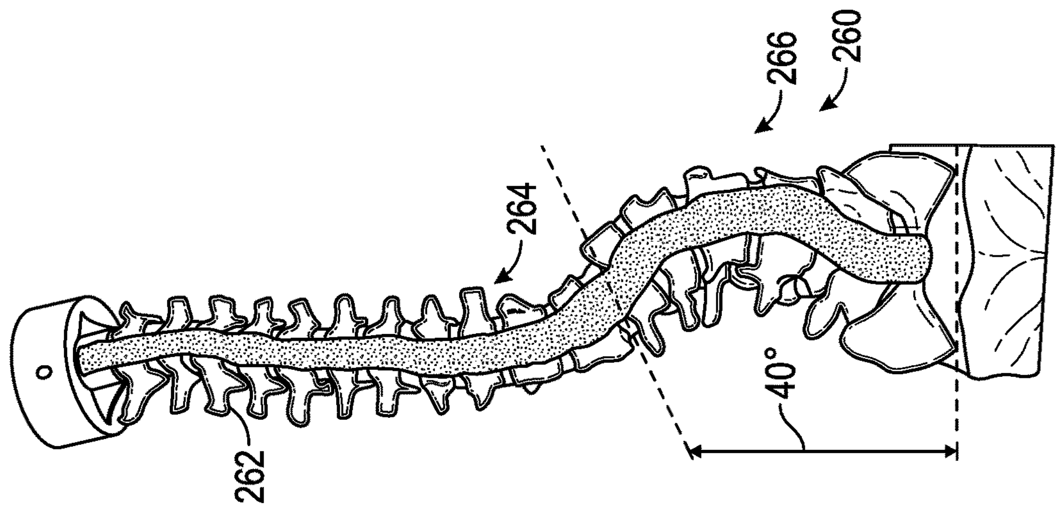
FIG. 2C is an image of a synthetic spinal segment printed to mimic certain predefined anatomic, biomechanical, and physiological properties of the reference spinal segment of FIG. 2B.
Figure 2B:
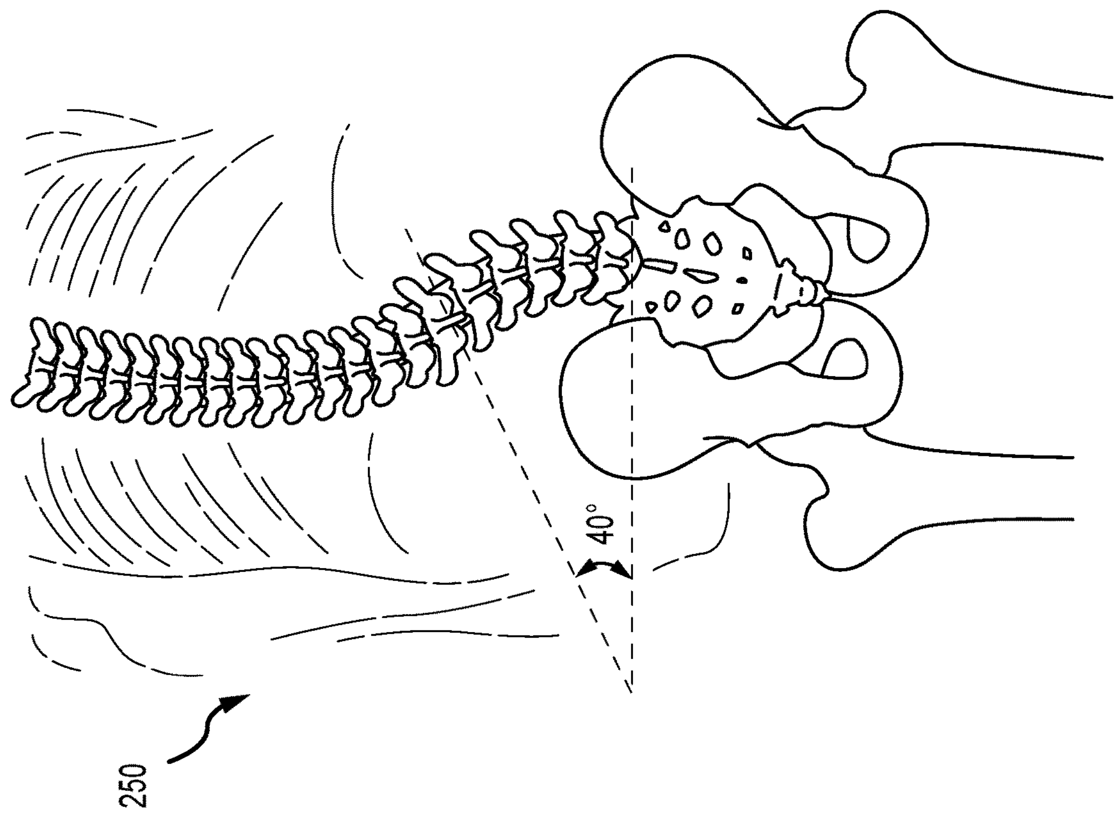
FIG. 2B is a radiograph view of a reference anatomical component (spinal segment).

Referring again to FIG. 2B and referring to FIG. 2C, the (printed) synthetic anatomical model 116 may include a printed synthetic spinal segment model 260 created using image data in the form of a high-resolution computed tomography of the same patient associated with the reference spinal segment 250, and formed to resemble or mimic the reference spinal segment 250. The synthetic spinal segment model 260 may be printed with different portions having different simulated/synthetic anatomical, physiological, or biomechanical properties. As shown, for example, the synthetic spinal segment model 260 printed based on the reference spinal segment 250 may be printed to include at least a first portion 262, a second portion 264, and a third portion 266. The first portion 262 may be printed according to a first printing configuration (with e.g., certain materials and print parameters), the second portion 264 may be printed according to a second printing configuration (with e.g., certain materials and print parameters which may differ from the materials and print parameters of the first configuration), and the third portion 266 may be printed according to a third printing configuration (with e.g., certain materials and print parameters which may differ from the materials and print parameters of the first/second configurations). In other words, the synthetic spinal segment model 260 may be printed with synthetic bone that mimics the bone of the reference spinal segment 250 with respect to gross anatomy, radiographic anatomy, and biomechanical performance when instrumented with pedicle screws. The synthetic spinal segment model 260 may also be printed with intervertebral discs (first portion 262), an anterior longitudinal ligament (second portion 264), and a posterior longitudinal ligament (third portion 266) so that the relative flexibility of the synthetic spinal segment model 260 mimics the flexibility of the patient associated with the reference spinal segment 250.

Figure 2E:
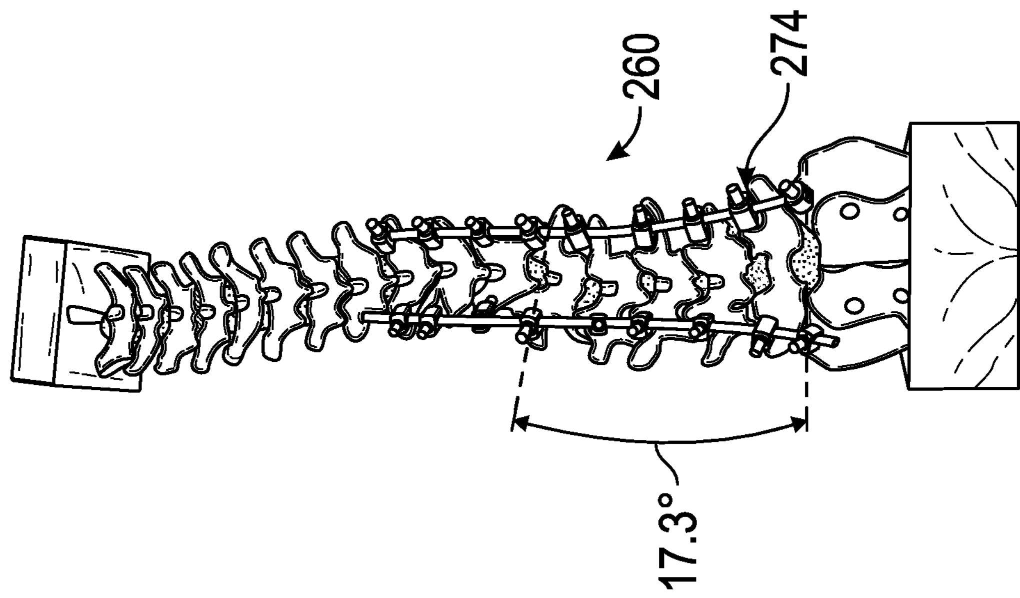
FIG. 2E is an image of the synthetic spinal segment of FIG. 2C after simulated surgical correction.
Figure 2D:
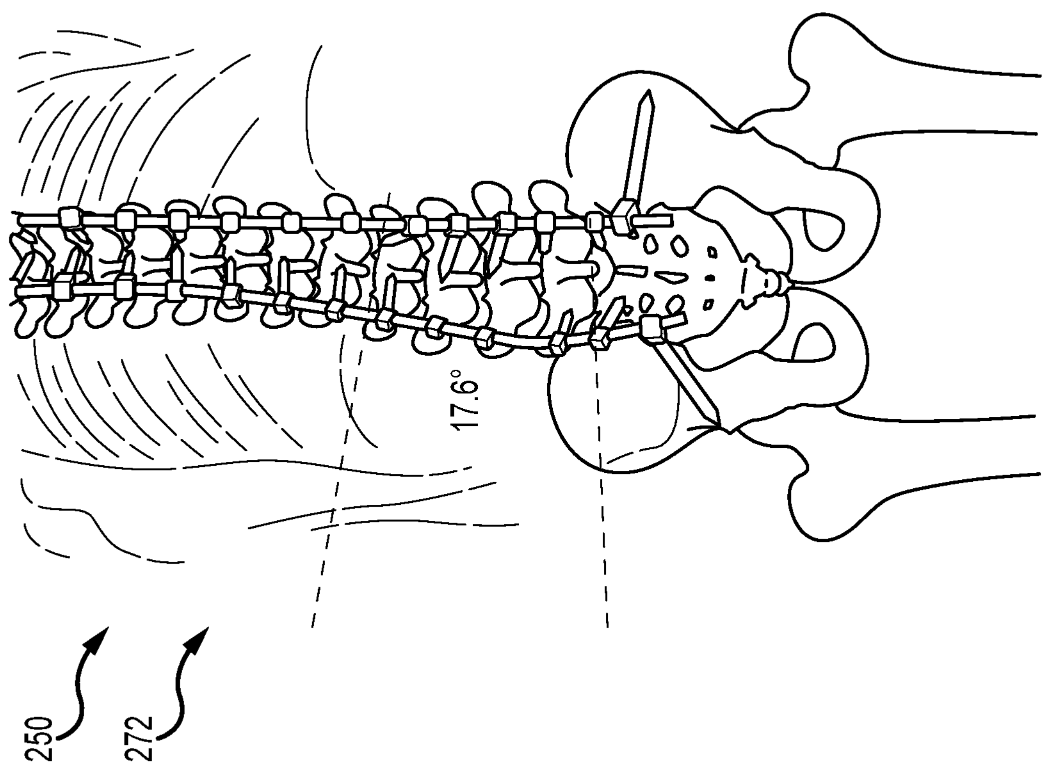
FIG. 2D is a radiograph image of the reference spinal segment of FIG. 2B after surgical correction.
Figure 3:
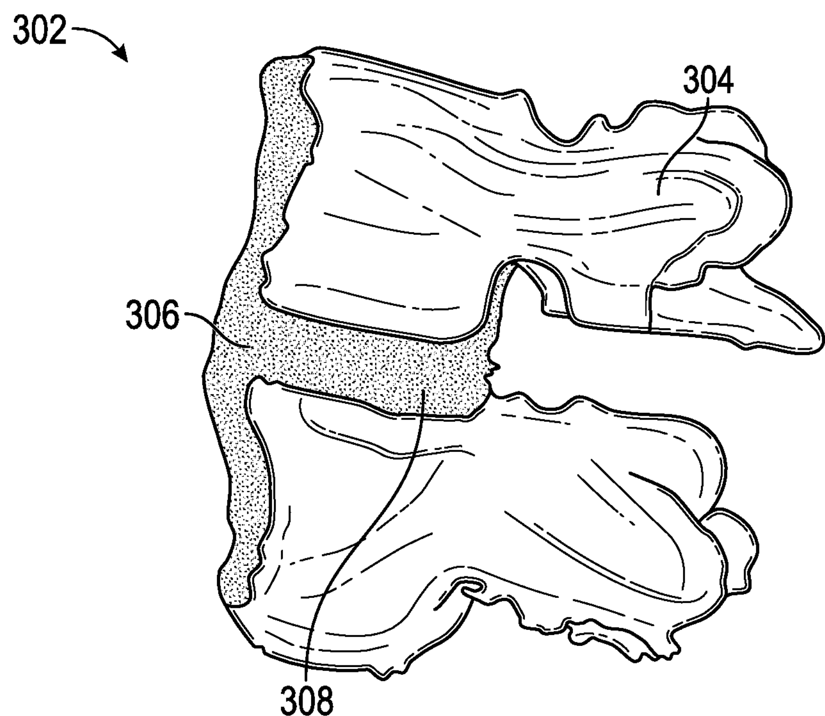
FIG. 3 is a side view of a synthetic spine model constructed according to the method described in FIG. 2A and discussed herein.
Figure 4:
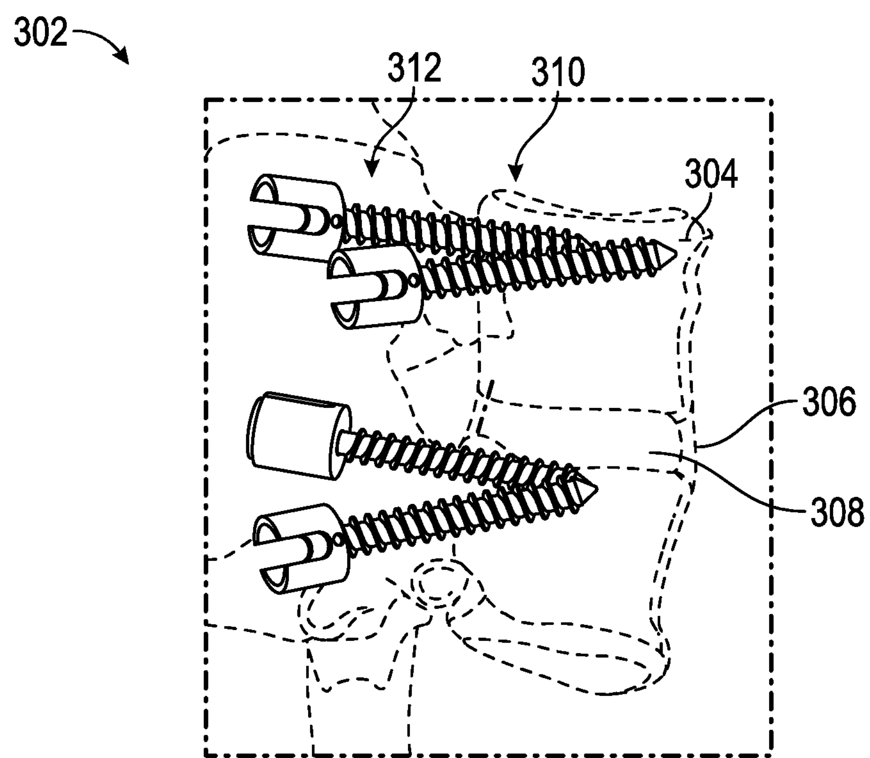
FIG. 4 is a lateral view of an X-ray taken of the same spine model referred to in FIG. 3 after pedicle screw placement.
Figure 5:
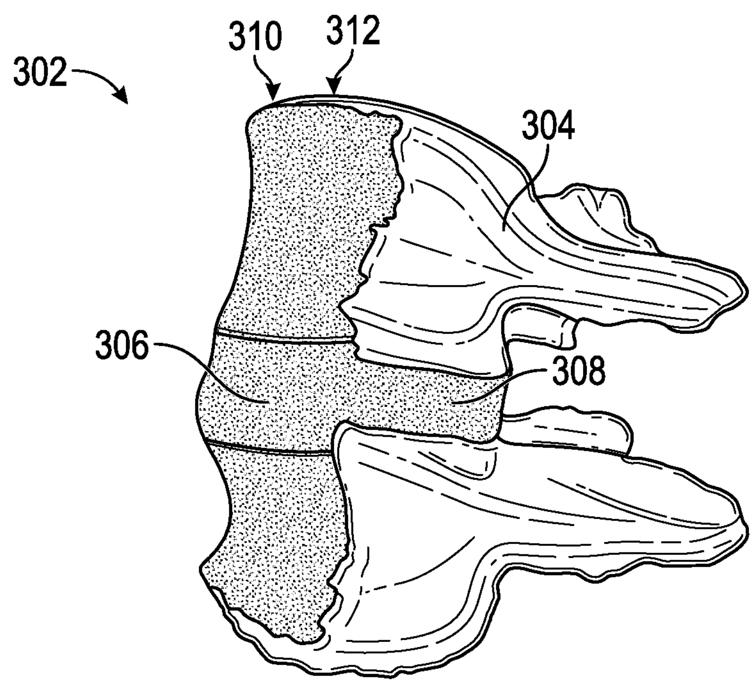
FIG. 5 is an anterolateral view of the same model in FIG. 3, demonstrating the different 3D printed materials representing and biomechanically performing as bone (white), anterior longitudinal ligament (black), and annulus fibrosis (black).
Figure 6:
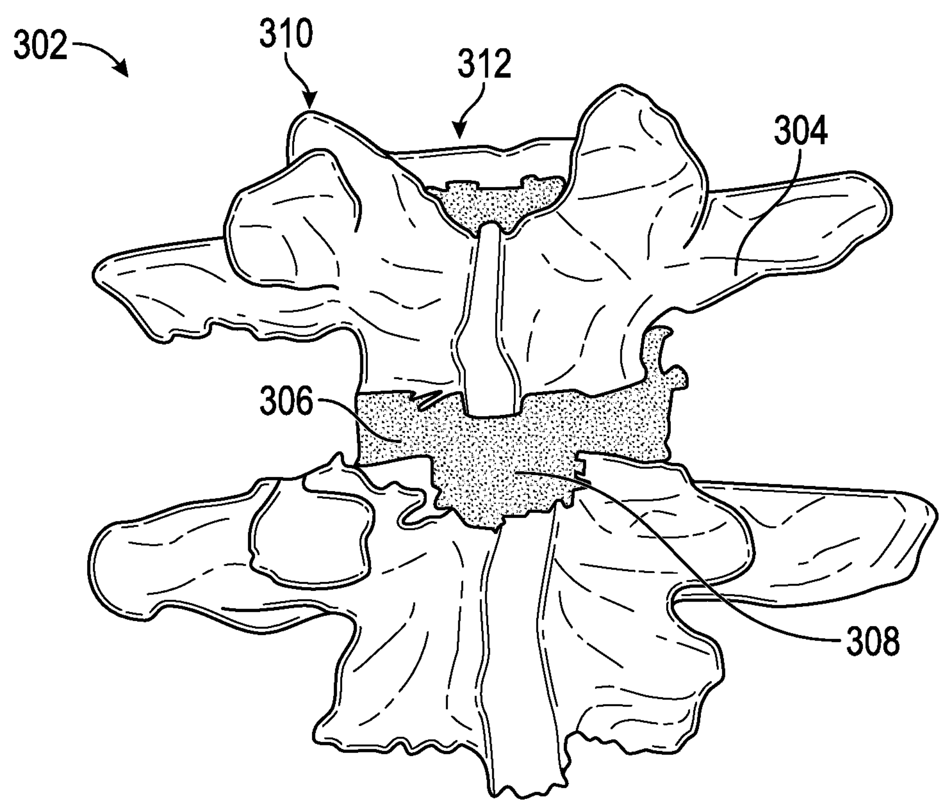
FIG. 6 is a posterior view of the same model in FIG. 3, demonstrating the different 3D printed materials representing and biomechanically performing as bone (white), and posterior longitudinal ligament (black). In this model the facet joints have been removed to simulate a posterior column osteotomy.

Referring to FIGS. 2D-2E, the synthetic anatomical model 116 may be utilized for training, preparation, or other applications such as the simulation of surgical correction. In FIG. 2D, surgical correction has been applied to the reference spinal segment 250 using a spinal fixation construct 272. Similarly, a spinal fixation construct 274 has been applied to the synthetic spinal segment model 260. The spinal fixation construct 272 may be the same or similar construct as the spinal fixation construct 274, so that surgical correction of the reference spinal segment 250 may be simulated using the synthetic spinal segment model 260 and the spinal fixation construct 274. As shown, the remaining curve left over after surgical correction has been applied to both of the reference spinal segment 250 and the synthetic spinal segment model 260 is similar in value, which demonstrates that the synthetic spinal segment model 260 has been constructed advantageously with similar properties to that of the reference spinal segment 250 and therefore provides a suitable tool for education and surgical preparation.

As another specific example, referring to FIGS. 3-6, a non-limiting embodiment of a printed spinal segment 302 is illustrated that has been 3D printed in parts or in whole using the method of FIG. 2A for constructing an anatomical model with anatomic and biomechanical fidelity to a cadaveric spine model. In this embodiment, the printed spinal segment 302 is constructed with biocompatible materials configured to have physical and chemical properties that may enable the spinal segment 302 to be integrated with natural anatomy. Specifically, the printed spinal segment 302 includes printed components such as biomechanically performing bone (304), anterior longitudinal ligament (306), and annulus fibrous (308). Each of these components may be printed according to different specific configurations of printing materials and printing parameters in order to simulate natural anatomy for each component. In addition, although not shown, the spinal segment 302 may be printed with cavities configured to receive pedicle screws. It is noted that the segment need not be printed with complete anatomical accuracy to be suitable for use. The size, placement, and orientation of the pedicle screw cavities can be determined by the user in one non-limiting embodiment of this method, or indeed, it can be decided by a computer algorithm. Other components can be incorporated into the pedicle screw cavity, such as threading, drill stops, and other components or characteristics that the user could desire. It is also contemplated that a set or a single pedicle screw (not shown) could be printed along with the spinal segment 302 and then be installed and held in place by threading mechanisms, adhesives, fusing, or any other attachment mechanism without departing from the scope of the disclosure. It is also considered, that the cavities could be drilled separately, and the pedicle screws or other components could be 3D printed individually. With this model, the spinal segment 302 has had posterior column osteotomies performed upon it.

Ultimately, the user may design the structure and condition of the synthetic anatomical model 116 according to any desired customizations to accommodate factors such as cost, printing time, research purposes, or any other relevant purpose without departing from the scope of the disclosure. For example, the synthetic anatomical model 116 may be printed in a configuration that mimics a spinal deformity. In this instance, the testing procedure may be modified to include the same techniques and instruments that would be customary for the specific intraoperative procedure, where the specific structure of the spinal deformity may be abnormal in nature, in order to mimic patient spinal deformities such as, but not limited to, spondylolisthesis and scoliosis. In addition, as described, many suitable variants of printing or building materials may be used. The user may modify, during the aforementioned steps of process flow 200 or after, the type of printing material, the amount of printing material used, and any other combination of parameters suitable for the user's needs. In addition, additives may be added to the printing reservoir of the 3D printer 106 to impact the physical and chemical properties of the printed component. For example, anti-microbial solutions may be added to the printing material so that the final synthetic anatomical model 116 may have anti-microbial properties suitable for medical purposes. Moreover, the method of process flow 200 may include supplementary printing processes to complete the printed synthetic anatomical model 116. To illustrate, the instant non-limiting method could include a stereolithographic step, a fused deposition modeling step, an electron beam additive manufacturing step, a selective laser melting step, a selective laser sintering step, or any combination of these steps without departing from the scope of the disclosure. It is further contemplated that the printing process described in FIG. 2A could take place in a sterile environment. For instance, the 3D printer 106 could be placed in a hood, or any environment with high-efficiency particulate air (HEPA) filtration configured to maintain sterility. The process flow 200 may also include a cooling step that allows the component to retain its printed shape.

Referring to block 212 of FIG. 2A, additional synthetic components (shown in FIGS. 18-26) may be constructed which may be integrated with the synthetic anatomical model 116, or separately formed/used (as described herein) for different applications during a post processing step 150 or stage. The additional synthetic components formed during a post-processing step 150 may include a synthetic thecal sac, blood vessels, nerve roots, various types of soft tissue, synthetic dermis, subcutaneous adipose tissue, paraspinal muscles, and supportive ligament structures of the spine or other components. The additional synthetic components may be useful to simulate blood loss through synthetic bone (of the synthetic anatomical model 116), bleeding from direct vessel injury, monitoring of electrical signals through synthetic neural elements, monitoring of pressure in particular parts of the synthetic anatomical model 116 such as the thecal sac to provide feedback on potential for neural element injury during a particular surgical maneuver, and provide radiographic feedback from the synthetic anatomical model 116 to under standard radiographic image processes such as fluoroscopy or computed tomography. Such additional synthetic components may be integrated or formed with the synthetic anatomical model 116, during construction of the synthetic anatomical model 116, constructed separately before or after the construction of the synthetic anatomical model 116, and integrated with the synthetic anatomical model 116 after formation.

Referring to block 214 of FIG. 2A, the synthetic anatomical model 116 may undergo or be subjected to various testing procedures. For example, the synthetic anatomical model 116 may be subjected to controlled and measured forces, or to instrumentation, through a variable system of cables, pulleys, belts, motors, and weights, all the while measuring the spinal range of motion using an optical tracking system, and the forces applied to the spine using mechanical force sensors. Various measurements taken during testing may include, but are not limited to, the spine range of motion on flexion, extension, side-bending, and axial rotation, axial screw pullout strength, maximum torque on spinal screw insertion, and numerous others. Analysis of these measures post-testing may inform whether the 3D printing model for the synthetic anatomical model 116 should be adjusted by e.g., applying modifications to the image features of the 3D printing file, or by modifying print parameters and materials selection. As indicated in FIG. 2A, the process of testing the synthetic anatomical model 116 and adjusting print settings may be repeated as desired.

Figure 7:
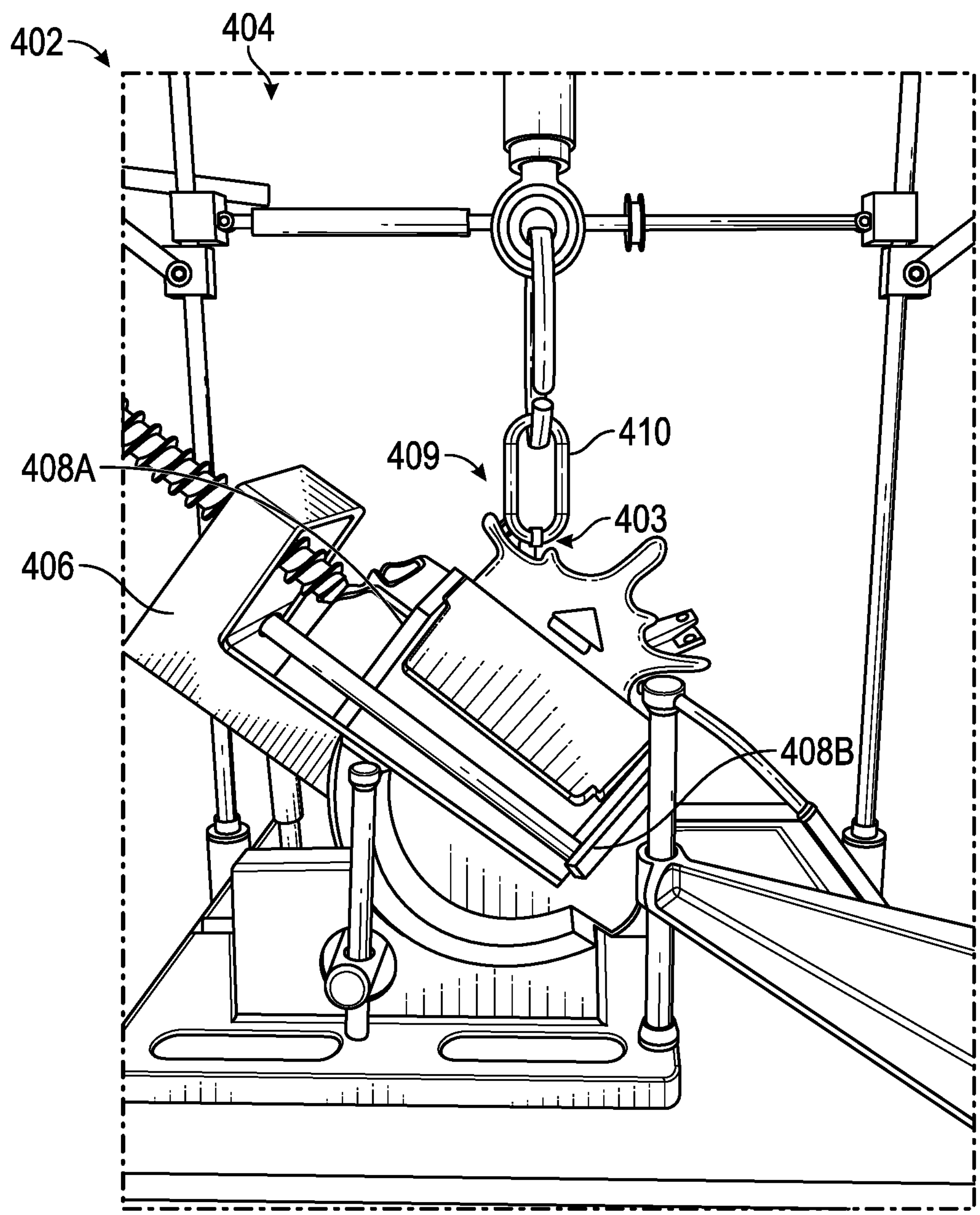
FIG. 7 is an image illustrating biomechanical testing of a vertebral body model, specifically axial screw pullout strength testing. This testing contributed to the experimentally derived protocols for configuring or selecting specific print parameters to mode specific healthy or diseased bone states.
Figure 8:
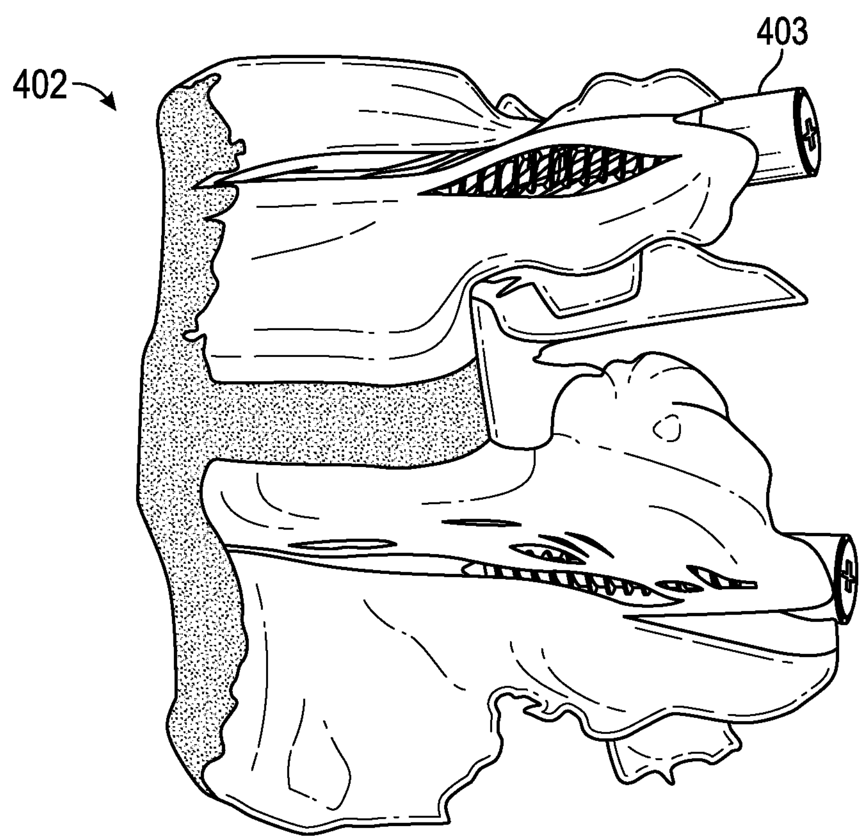
FIG. 8 is a lateral view of the same spine model referred to in FIG. 3 after pedicle screw insertion and biomechanical testing of pedicle screw and intervertebral disc compression.
Figure 9:
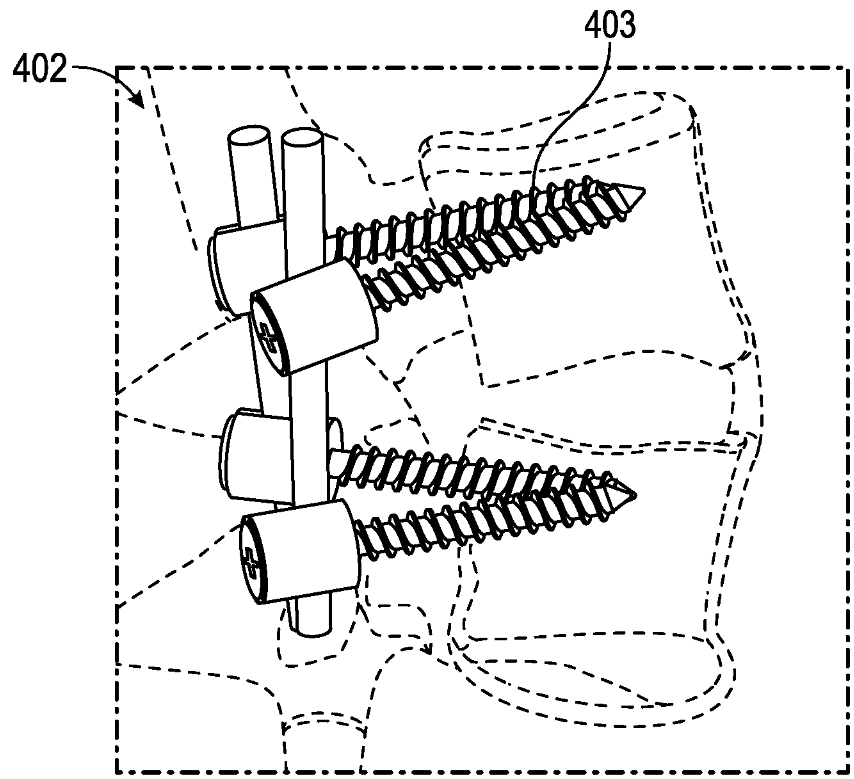
FIG. 9 is a lateral X-ray taken of the same spine model referred to in FIG. 8 at the time of biomechanical testing of pedicle screw and intervertebral disc compression.

FIGS. 7-9 illustrate testing of a vertebral body model 402 relative to at least one pedicle screw 403, specifically, axial screw pullout strength testing using a testing apparatus 404 having a vise grip 406. This testing contributed to the experimentally derived datasets 112 for configuring or selecting specific print parameters to mode specific healthy or diseased bone states. The vise grip 406 is arranged to provide a true axial force on the pedicle screw 403 as described herein. FIG. 8 is a lateral view of the same spine model referred to in FIG. 3 after biomechanical testing of pedicle screw and intervertebral disc compression. This model demonstrates pedicle fractures as a result of over-compression, similar to what was seen in the cadaveric studies that FIG. 3 was modeled after.

Referring again to FIG. 7, the testing apparatus 404 is arranged to provide a true axial force on the pedicle screw 403 as described herein. The duration, time, and type of testing may be controlled by the user or a computer algorithm per predetermined testing parameters that are generated for specific circumstances suitable for the user's needs. Devices such as the testing apparatus 404 implemented for conducting the testing may be configured by the user or a computer algorithm, and can take any form necessary to suite the user's preferences. In the instant non-limiting embodiment, the vertebra body model 402 is disposed between the jaws 408A and 408B of the vise grip 406 and a top portion 409 of the pedicle screw 403 and/or the vertebra body model 402 is configured to attach or otherwise engage to a carabiner 410 such that a user may exert external force on the pedicle screw 403 and/or the vertebra body model 402 to test its resistance to changes in pressure, force, angle, and other factors that may be mirrored by its use in the patient's spine. It is of course contemplated that other testing may be undergone, such as radiation testing, kinematics testing, and any other testing that would suit the user's preferences. The instant non-limiting method of the disclosure may also be used on animal parts, or non-living components. For example, it is contemplated that a spine of a canine may be used in testing, training, and demonstration.

Figure 10:
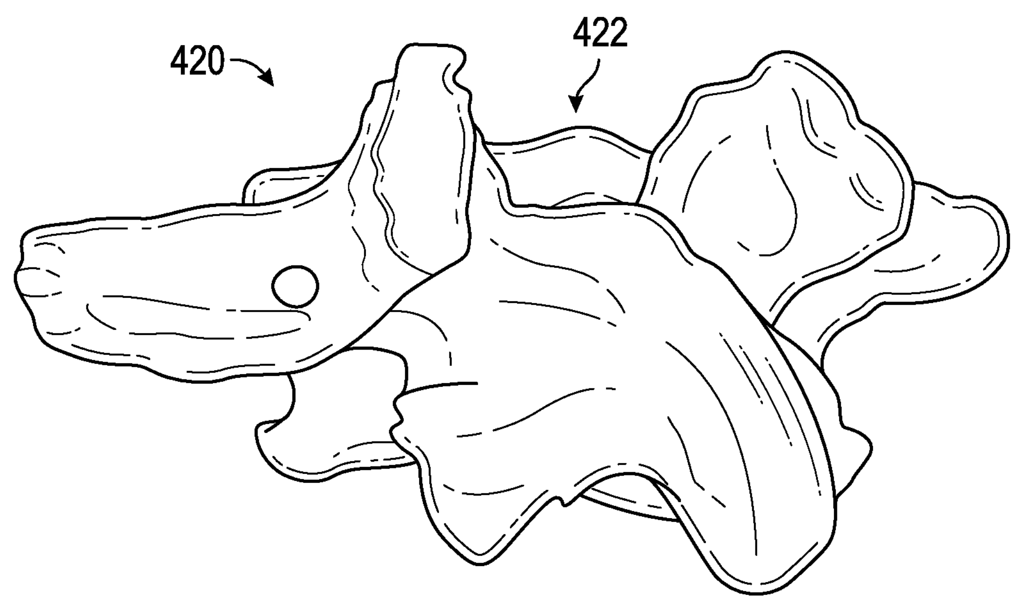
FIG. 10 is an image illustrating a 3D printed vertebral body model with pre-determined cannulation trajectories of the vertebral pedicle.
Figure 11:
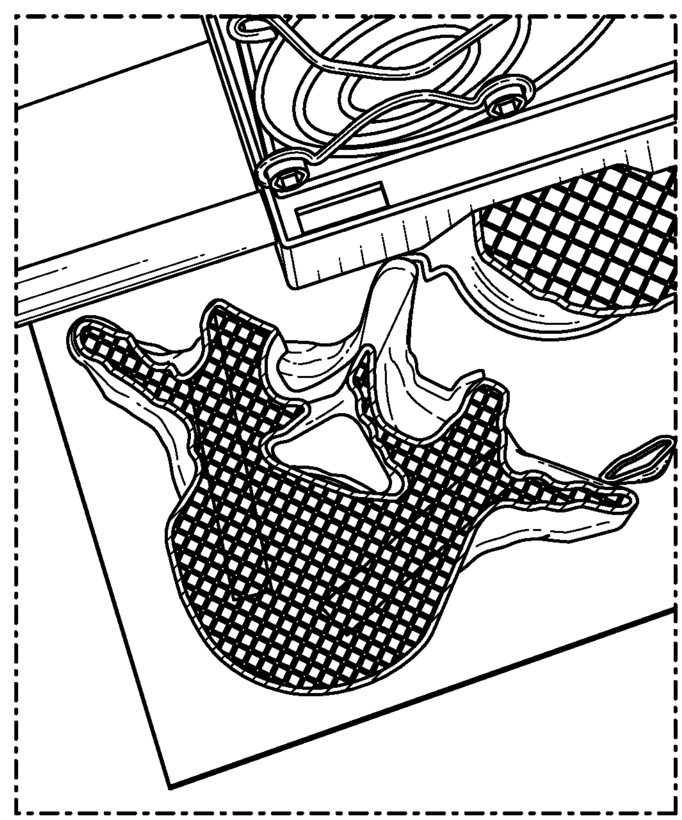
FIG. 11 is an image illustrating a synthetic vertebral body model that is being printed to include pedicle cannulation trajectories.

FIG. 10 illustrates a 3D printed vertebral body model 420 with pre-determined cannulation trajectories 422 of the vertebral pedicle. This eliminates variability in the trajectory of pedicle screws, and thereby reduces the variability in biomechanical testing achieved when using the synthetic models. Consequently, this model demonstrates a significant advantage over cadaveric vertebral bodies or other synthetic bone and spine models. FIG. 11 illustrates a synthetic vertebral body model that is being printed to include pedicle cannulation trajectories. This image also demonstrates how the models are printed to mimic the corticocancellous architecture of human bone, with a thick cortical outer shell, and a thinner mesh filing the interior of the model. This architecture provides both high fidelity radiographic anatomy of the model under standard fluoroscopy and computed tomography, enables certain physiological functions such as bleeding of the bone (after modification are made post-printing), and improves the biomechanical performance of the bone as it more closely mimics the architecture of human bone.

Experimentally Derived Datasets 112

As described, the experimentally derived datasets 112 are informative as to suitable configurations for printing materials and print parameters to print anatomical models with predetermined properties. Substantial research and testing was conducted to arrive at the experimentally derived datasets 112. Specifically, for example, at least one study was conducted to describe the biomechanical performance of a three-dimensional (3D)-printed vertebra on pedicle screw insertional torque (IT), axial pullout (APO), and stiffness (ST) testing. Seventy-three anatomically identical L5 vertebral body models (146 pedicles) were printed and tested for IT, APO, and ST using single-threaded pedicle screws of equivalent diameter (6.5 mm), length (40.0 mm), and thread pitch (2.6 mm). Material, cortical thickness (number of shells), cancellous density (in-fill), in-fill pattern, and print orientation were varied among the models. One-way analysis of variance was performed to evaluate the effect of the variables on the outcomes.

SUMMARY

During the study, it was found that the type of printing material significantly affected IT, APO, and ST ($P<0.001$ for all comparisons). For acrylonitrile butadiene styrene (ABS) models, in-fill density (25-35%) had a positive linear association with APO ($P=0.002$), ST ($P=0.008$), and IT ($P=0.10$); similarly for the polylactic acid (PLA) models, APO ($P=0.001$), IT ($P<0.001$), and ST ($P=0.14$). For the nylon material type, in-fill density did not affect any tested parameter. For a given in-fill density, material, and print orientation, the in-fill pattern had a significant effect on IT ($P=0.002$) and APO ($P=0.03$). Print orientation also significantly affected IT ($P<0.001$), APO ($P<0.001$), and ST ($P=0.002$). The 3D-printed vertebral body models made of ABS and PLA performed analogously to human bone on pedicle screw tests of IT, APO, and ST. By altering the material, in-fill density, in-fill pattern, and print orientation of the synthetic vertebral body models, one could reliably produce a model that mimics bone of a specific bone mineral density.

Detailed Testing and Analysis

Additional details regarding the research and testing associated with a 3D-printed spine model, which contributed at least in part to the formation of the experimentally derived datasets 112, shall now be disclosed. Leveraging this research and the experimentally derived datasets 112, a synthetic spine model was eventually formed with synthetic bone material that mimics human bone in its corticocancellous architecture and its biomechanical performance on screw insertional torque (IT), axial pullout (APO) force, and stiffness (ST) testing. The model demonstrated expected changes in these biomechanical performance measures when printed to mimic human bone of higher or lower BMD.

As part of preliminary analysis, a high-resolution computed tomogram (CT) of a normal lumbar spine was segmented and converted into a 3D file using Materialise Mimics software (Materialise, NV, Leuven, Belgium). A complete L5 vertebra was extracted from this 3D file and converted to a stereolithography (.stl) file format. The .stl file was imported into the Simplify3D software package (Simplify3D, LLC, Blue Ash, Ohio, USA). A plurality of L5 vertebra models ("models") were then printed using a FlashForge Creator Pro.

During and after formation, the models were used to evaluate various 3D print settings suitable for a synthetic spine, including settings associated with base materials for 3D printing. By non-limiting example, the models were printed using three different materials: acrylonitrile butadiene styrene (ABS), polylactic acid (PLA), and nylon. ABS is a common thermoplastic polymer that is petroleum-based and known for its impact resistance and durability. PLA is a biodegradable and bioactive thermoplastic derived from sugar-based substances (e.g., cornstarch, sugarcane, cassava root). PLA has a much lower glass transition temperature than ABS and is more brittle, but it also has higher impact resistance and toughness. Nylon is a family of thermoplastic synthetic polymers. Nylon 230 may be implemented because it has a much lower glass transition temperature (230° C.) than other types of nylon. 3D-printed nylon is known for its high durability, strength, and versatility in that thin layers of printed nylon remain very flexible whereas thick layers become rigid and stiff.

Figure 12:
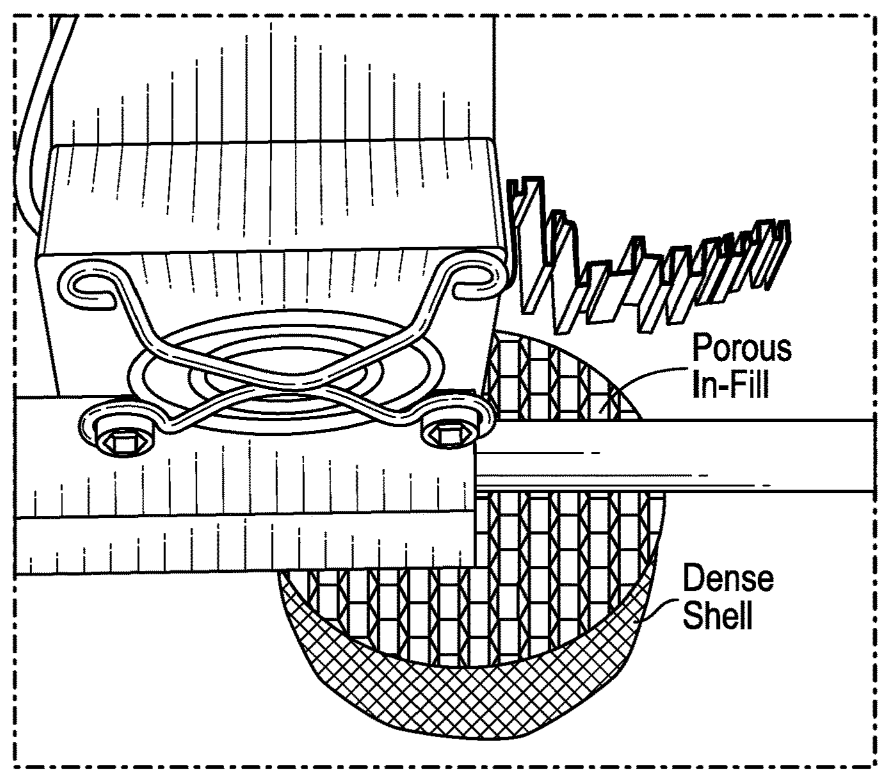
FIG. 12 is a top view illustrating a vertebral body associated with a synthetic spine model according to the present inventive concept where arrows denote the dense shell layers and less dense in-fill.
Figure 13:
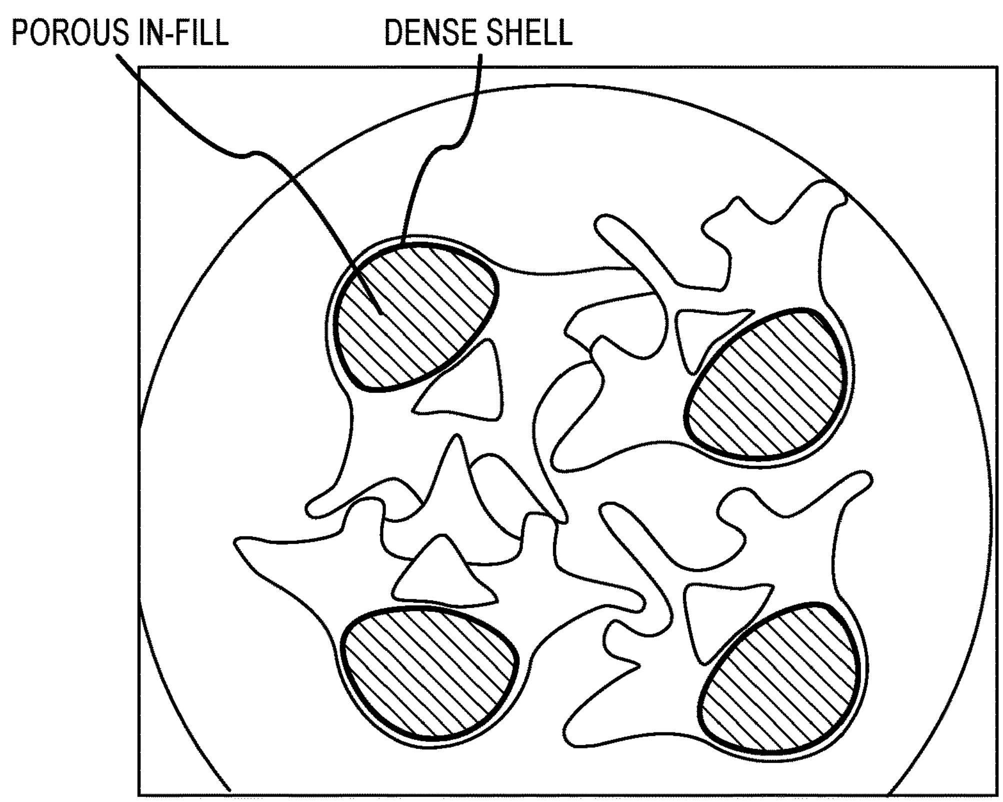
FIG. 13 is an axial view of a synthetic L5 vertebral body model under standard fluoroscopy and constructed using the methods described herein.

Other evaluated 3D print setting variables included print shell, in-fill percent, in-fill pattern, and print orientation, and the like. The 3D-printed L5 vertebral body models were printed with a dense outer layer of plastic (called the "shell") and a much less dense inner component (called the "in-fill"), analogous to the cortical and cancellous structure of human bone, respectively. FIGS. 12-13 demonstrate the shell and in-fill of a vertebral body model (FIG. 12), and how this structure mimics the cortiocancellous architecture of human bone when viewed under fluoroscopy (FIG. 13). It was discovered that both the shell and the in-fill can be modified to print at various thicknesses and densities. The in-fill can furthermore be modified to be printed in one of several different patterns, including hexagonal, diamond, and linear.

In one example study, a number of printer settings were held constant for all models printed with a specific material. For the ABS models, the print temperature was held at 240° C., the print bed temperature at 110° C., the print resolution at 0.2 mm, and the print speed at 60 mm/s. For PLA, the print temperature was held at 230° C., the print bed temperature at 30° C., the print resolution at 0.2 mm, and the print speed at 60 mm/s. For nylon, the print temperature was held at 230° C., the print bed temperature at 50° C., the print resolution at 0.2 mm, and the print speed at 30 mm/s. These printer settings were not tested for their effect on the biomechanical performance of the model; they were kept constant across all models printed with the same material in order to avoid any error introduced by variation in these settings.

Historical Results for Comparison

To validate the vertebral body model's utility as a synthetic bone substitute in biomechanical testing, historical data on cadaveric and living bone was referenced. Historical data included, e.g., comparison of the performance of a single-threaded vs a dual-threaded screw on IT, APO, and ST testing. This information was leveraged to implement similar methods to test the L5 synthetic vertebra models, using single-threaded screws of equivalent diameter (6.5 mm), length (40.0 mm), and thread pitch (2.6 mm). Screw insertion, IT, APO, and ST testing were all performed on the L5 synthetic vertebra models in order to permit a meaningful comparison of the results they generated using cadaveric bone with the results generated in this study using the synthetic L5 vertebra models. All equipment used in for this study during IT, APO, and ST testing was the same or similar equipment used by Brasiliense et al., as these studies took place in the same laboratory.

Study Design

Figure 14:
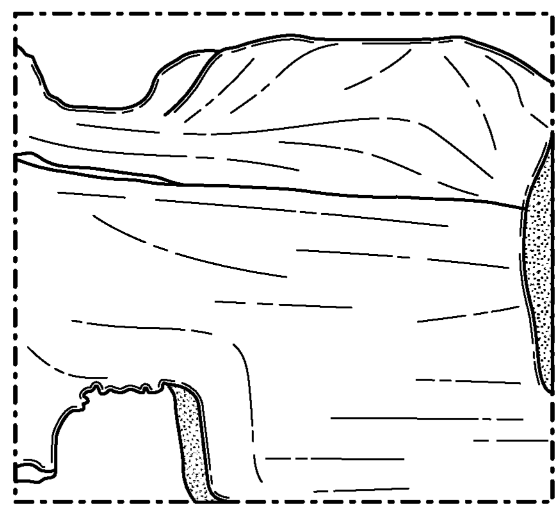
FIG. 14 is a photograph of a synthetic spine model constructed using the methods described herein with a horizontal orientation.
Figure 15:
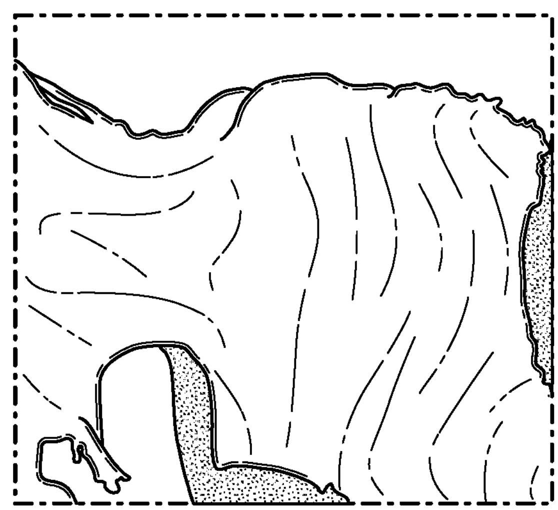
FIG. 15 is another photograph of a synthetic spine model constructed using the methods described herein with a vertical orientation.

Seventy-three L5 vertebral body models (146 pedicles) were printed from the same .stl file such that all the models were anatomically identical. ABS, PLA, and nylon models were printed with a shell density ranging from 1-8 shells, and an in-fill density ranging from 10%-50%. Models were also printed with different in-fill patterns (hexagonal vs. linear vs. diamond), and different orientations on the print bed (horizontal vs. vertical print alignment). FIG. 14 and FIG. 15 demonstrate the difference between models printed with horizontal print alignment and vertical print alignment. Horizontal and vertical refer to the z-axis of the 3D printer in relation to the anatomical top and bottom of the L5 vertebra. When the model is printed in the horizontal orientation (FIG. 14), layers of plastic filament are placed on top of each other from the bottom to the top of the vertebral model. In the vertical orientation (FIG. 15), filament layers are parallel to the top and bottom of the vertebra, and are stacked from the ventral vertebra to the dorsal vertebra.

Each model was subjected to pedicle screw insertion of the bilateral pedicles using a 6.5×40.0 mm screw with a single thread pitch of 2.6 mm. A tester inserted all the pedicle screws to minimize differences in pedicle screw trajectory between the models. To avoid bias, this tester was blinded to the torque values. During pedicle screw insertion, a torque sensor measured and collected the IT at a rate of 5 Hz. After bilateral pedicle screws were inserted in the models, they were placed in a metal fixture and potted in a casting mold of polymethyl methacrylate.

After the vertebral bodies were potted, a uniaxial servo-hydraulic test frame (858 Mini Bionix, MTS Test Systems Corp., Eden Prairie, Minn., USA) was used to conduct APO testing of each pedicle screw. In summary, an angle vise was used to affix the polymethyl methacrylate mold of each model to the base of the testing apparatus. The long axis of the pedicle screw to be tested was then aligned parallel to the axis of the testing apparatus in order to create a pure axial force vector on each pedicle screw. APO loading force was at a 10 mm/min displacement rate. Load versus displacement data were continuously recorded at a frequency of 10 Hz until total screw failure, which was defined as the point on the load-displacement curve at which a precipitous decline occurs. APO was then calculated as the greatest load prior to failure. The load-displacement curve was then used to calculate the screw ST, which was defined as the steepest slope on the load-displacement curve. Referring back to FIG. 7, the illustration shown demonstrates a vertebral body model undergoing such an APO test.

Statistical Analysis

Descriptive statistics, including means and standard deviations, were collected for all models. The D'Agostino-Pearson normality test was used to determine the normalcy of the data. Left and right pedicles were compared separately and together. One-way analysis of variance (ANOVA) tests were performed to evaluate for the effect of material, shell density, in-fill density, in-fill pattern, and print pattern on the measured outcomes.

Results

Thirty-seven ABS models were printed and underwent complete testing. These models had shell density ranging from 1 to 8 shell layers, in-fill density ranging from 10 to 50%, 3 different in-fill patterns (hexagonal, linear, diamond), and both horizontal and vertical print orientations. Twenty-seven PLA models and 27 nylon models were printed, all with a shell density of 4 or 8 layers and an in-fill density of 25%, 30%, or 35%.

Figure 16A:
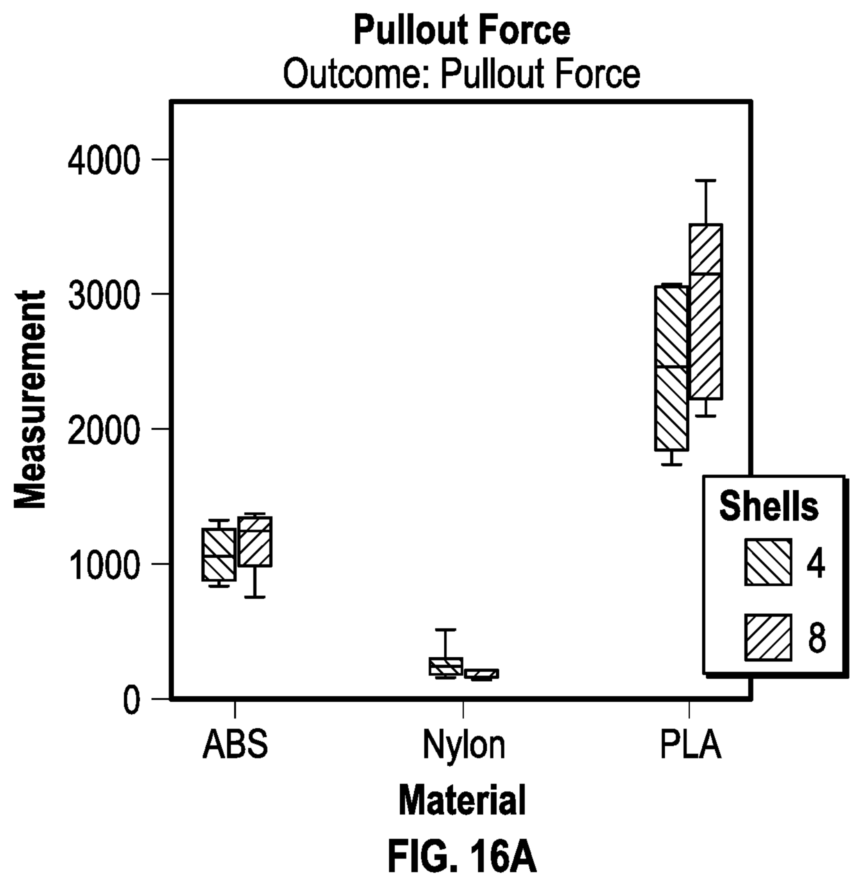
FIG. 16A-16C are box plot summaries demonstrating the effect of material type on the tested parameters.
Figure 16B:
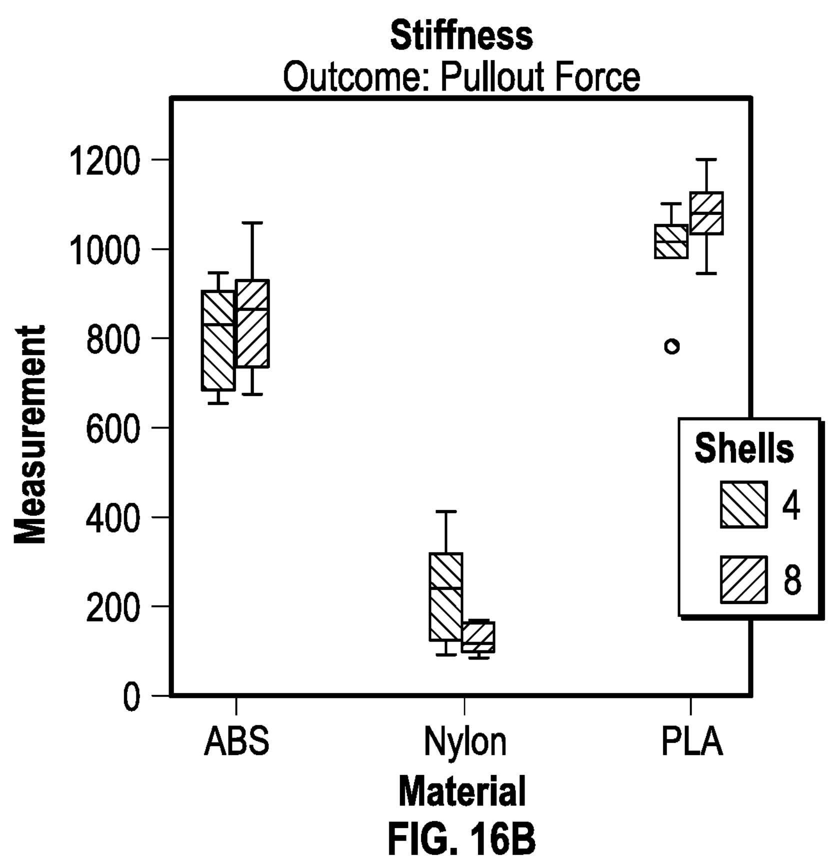
Figure 16C:
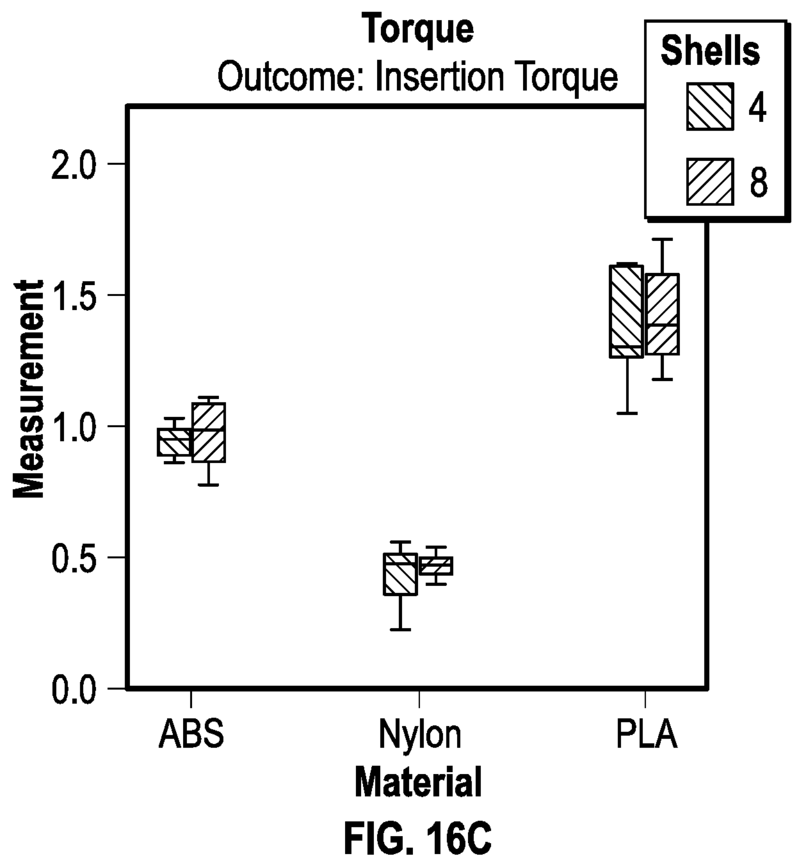
Figure 17A:
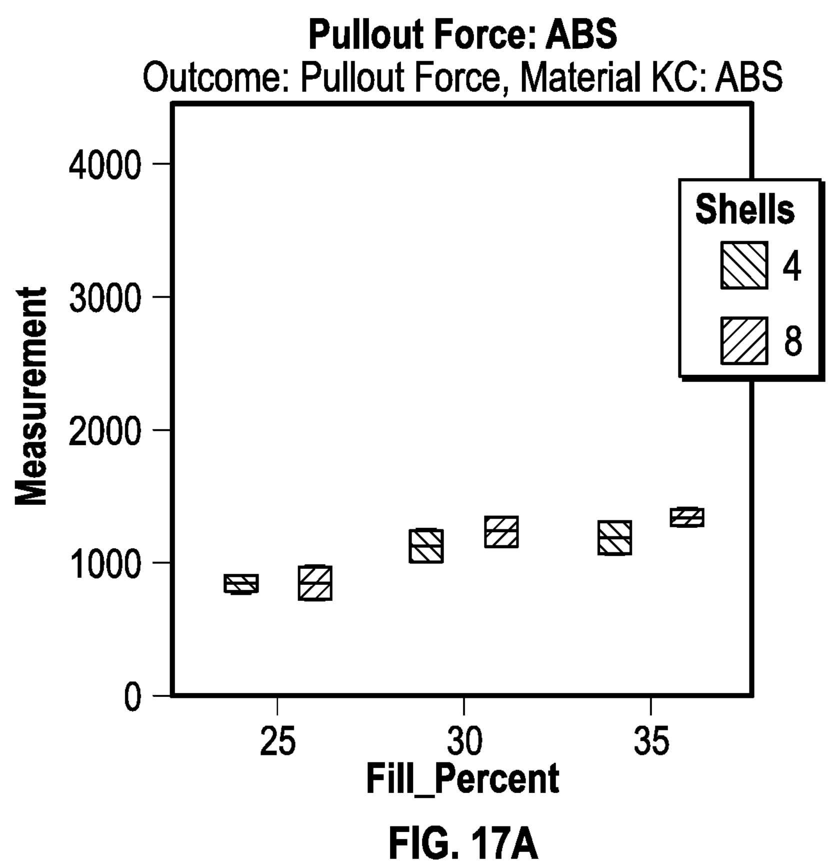
FIG. 17A-17I are box plot summaries demonstrating the effect of material and in-fill on the tested parameters.
Figure 17B:
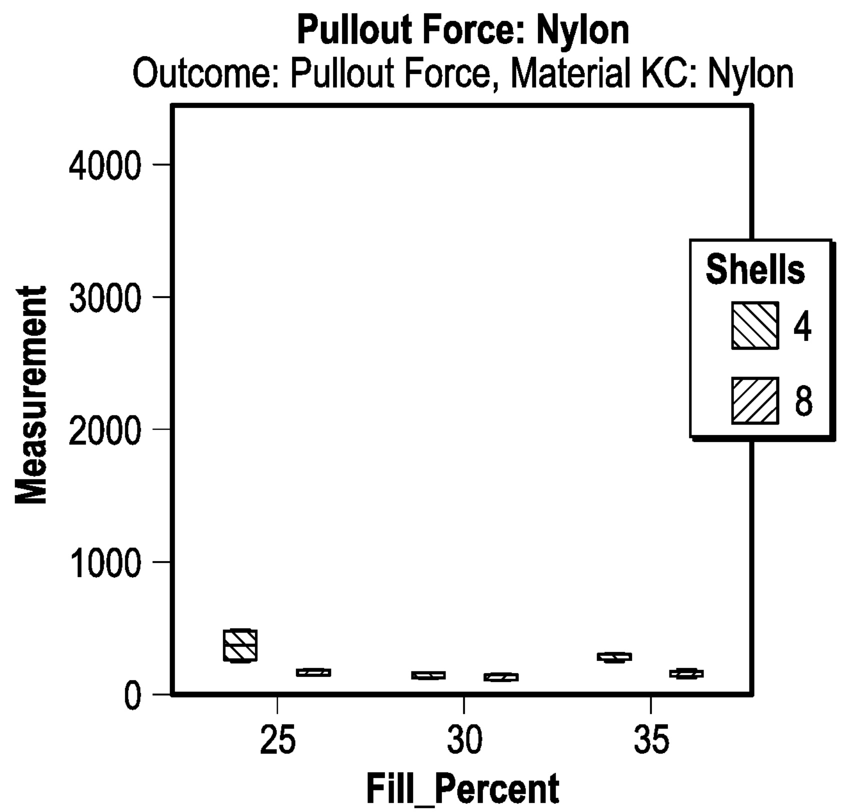
Figure 17C:
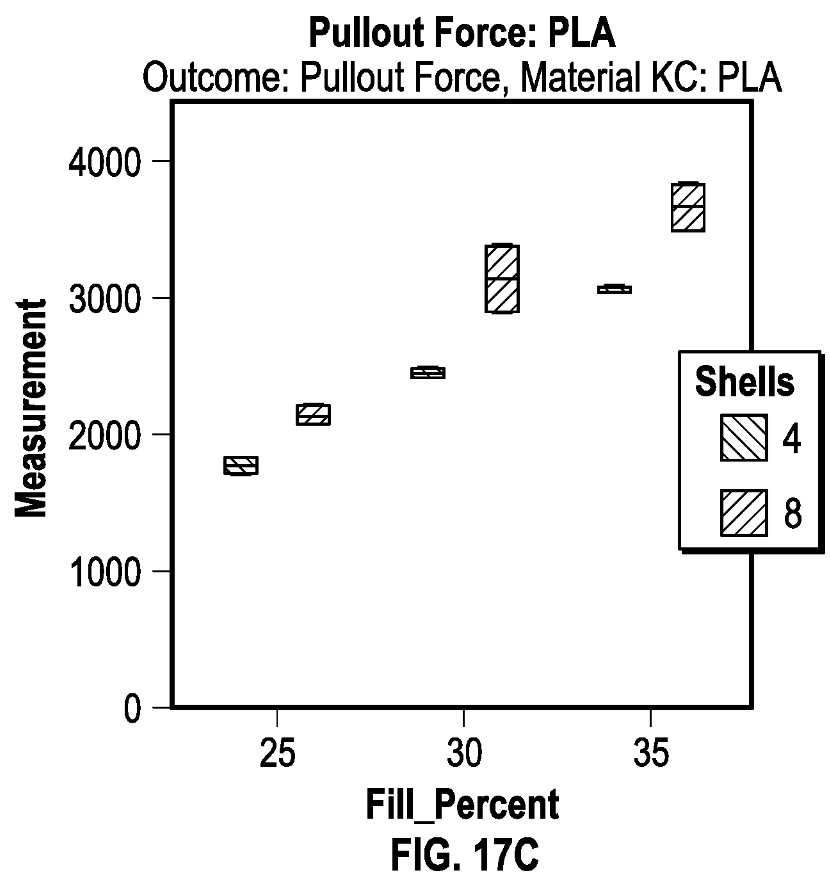
Figure 17D:
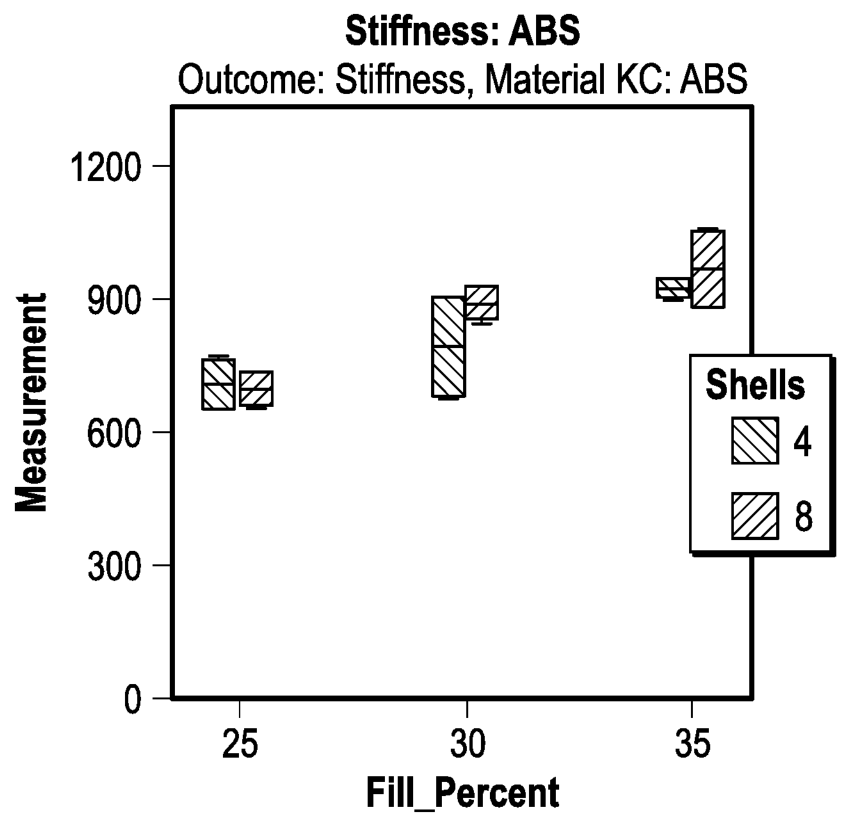
Figure 17E:
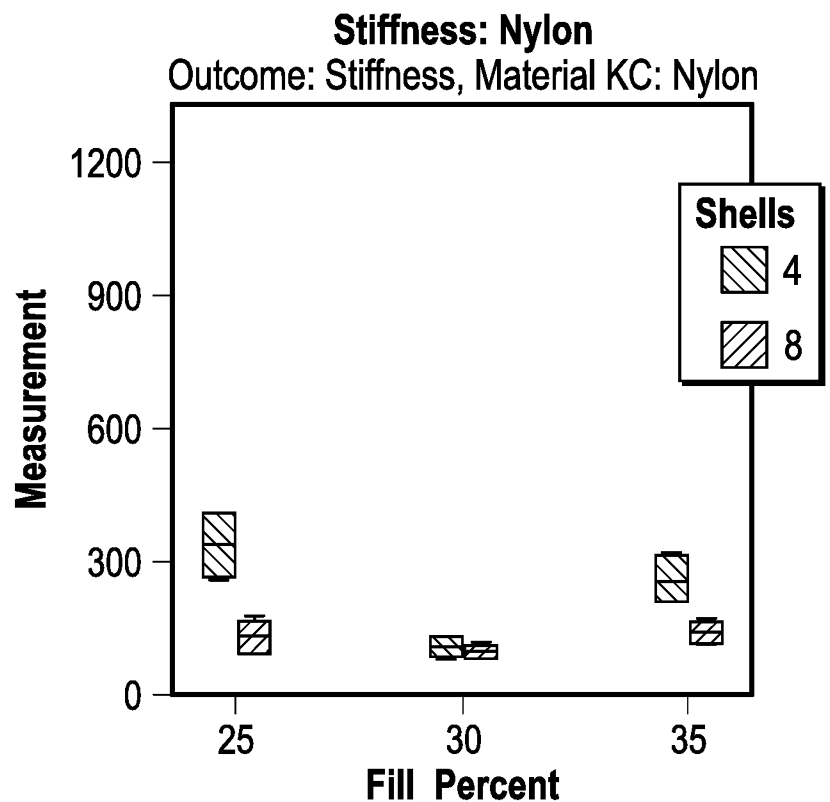
Figure 17F:
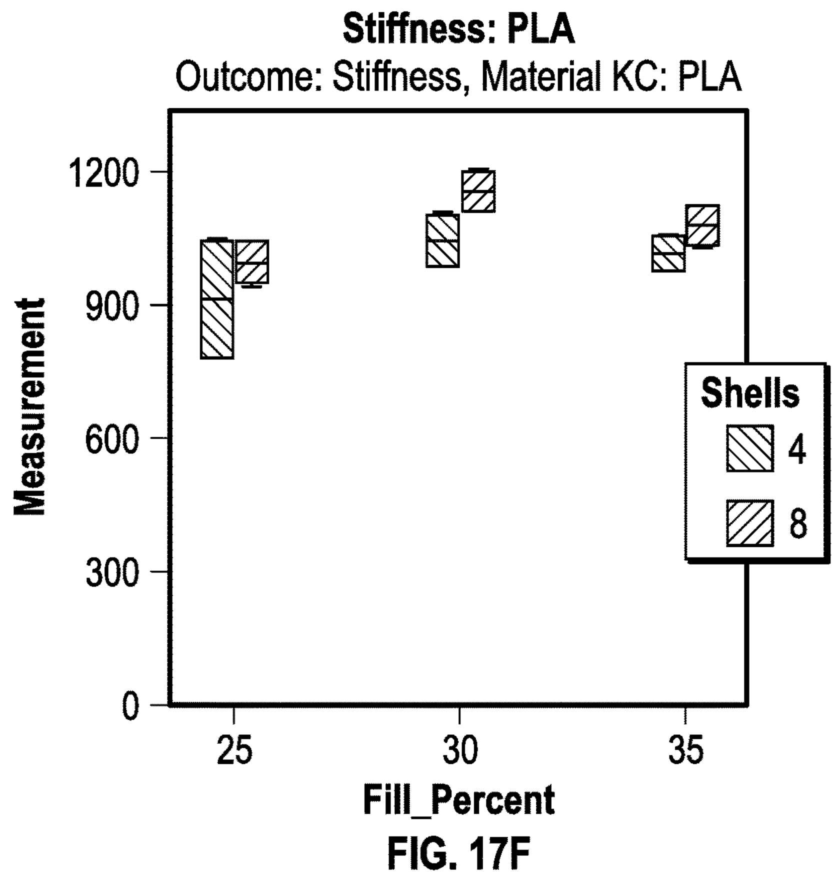
Figure 17G:
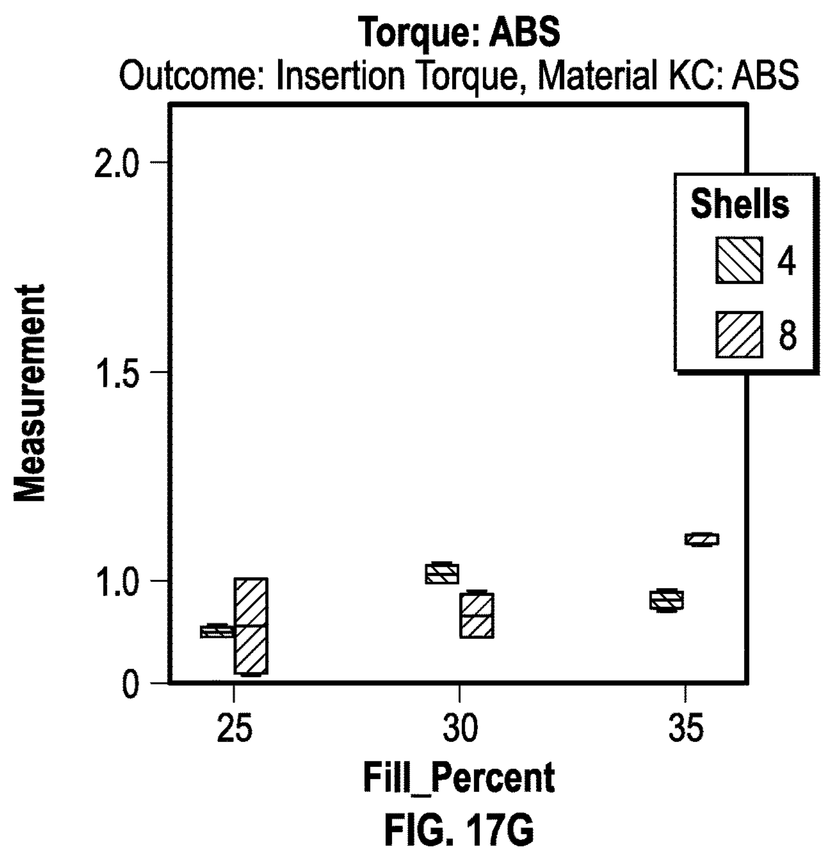
Figure 17H:
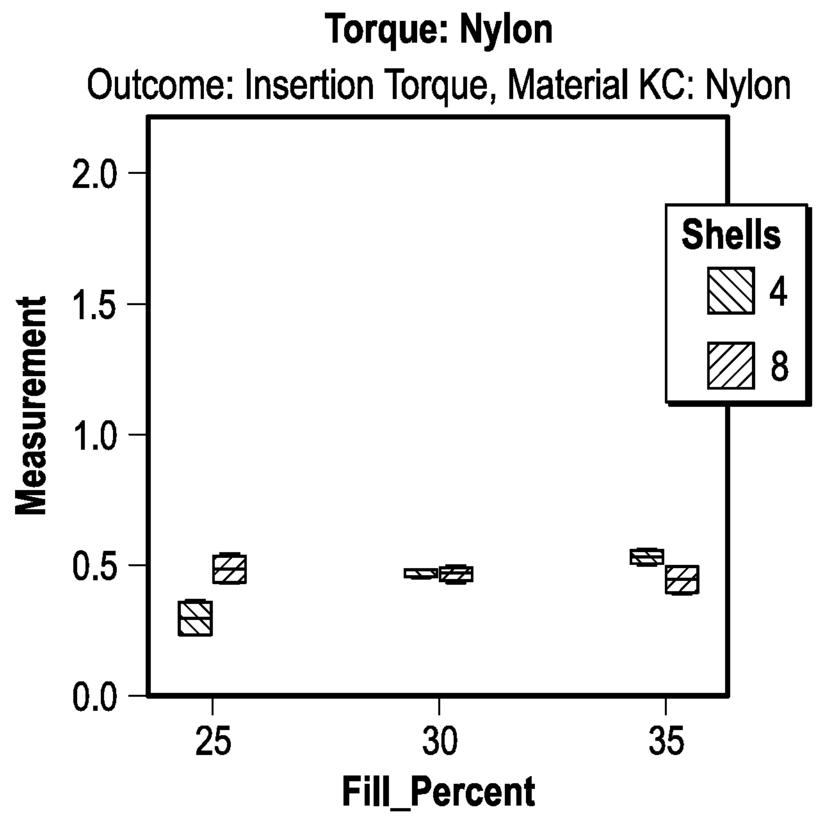
Figure 17I:
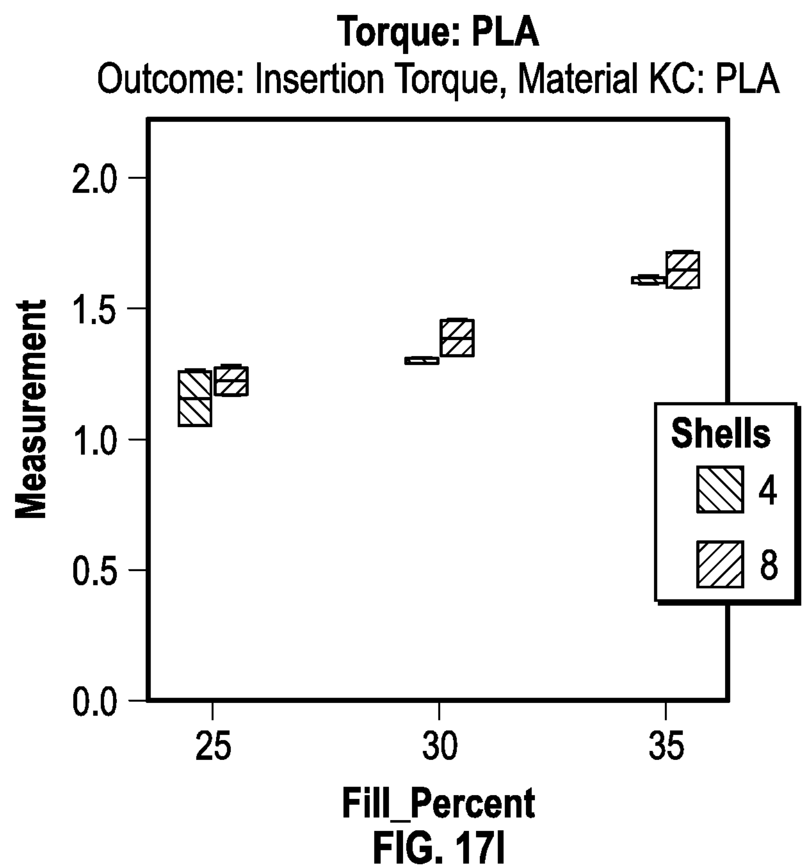

IT, APO, and ST tested values were normally distributed (D'Agostino-Pearson normality test, $P>0.05$ for all). In the analysis of all tested variables from all different material types, shells, in-fills, in-fill patterns, and orientations, no significant variance was found between pedicles on the left versus the right side for IT, APO, and ST ($P>0.05$ for all). The type of material significantly affected IT, APO, and ST ($P<0.001$ for all comparisons). FIG. 16 provides a box plot summary of the effect of material type on the tested parameters. The left box plot summary shows the effect of material type on axial pull-out (APO) testing; the middle box plot summary shows the effect of material type under stiffness (ST) testing; and the right box plot summary shows the effect of material type on insertional torque (IT) testing.

PLA demonstrated the highest IT, APO, and ST values, followed by ABS and nylon, respectively. For the ABS models, in-fill density (25-35%) had a positive linear association with APO ($P=0.002$), ST ($P=0.008$), and IT ($P=0.10$). For the PLA models, APO ($P=0.001$), IT ($P<0.001$), and ST ($P=0.14$) had a similarly positive linear association with in-fill density. For the nylon material type, in-fill density did not affect any tested parameter. FIG. 17 provides a box plot summary of the effect of in-fill on the tested parameters for models of all 3 material types: (Top row) Effect of in-fill on APO for ABS, Nylon, and PLA models; (Middle row) Effect of in-fill on ST for ABS, Nylon, and PLA models; and (Bottom row) Effect of in-fill on IT for ABS, Nylon, and PLA models.

For a given in-fill density, material, and print orientation, the in-fill pattern had a significant effect on IT ($P=0.002$) and APO ($P=0.03$) but not on ST ($p=0.23$). Print orientation also significantly affected IT ($P<0.001$), APO ($P<0.001$), and ST ($P=0.002$). Shell density did not significantly affect the biomechanical performance of the synthetic bone models.

Discussion of Results

Nylon does not appear to be a good material for a synthetic bone model, as changes in the evaluated print parameters did not result in predictable changes in the tested outcomes. ABS and PLA, however, demonstrated good correlation between model in-fill density and biomechanical performance measures, and as such both are good candidate materials for use in a synthetic lumbar vertebral body model. Interestingly, PLA models had significantly greater IT, APO, and ST values than ABS models. Anecdotally, however, the ABS models felt much more similar to human bone than the PLA models when cannulating the pedicles and placing pedicle screws. Specifically, the PLA did not break or deform under the pressure of a pedicle-finding probe, but rather became somewhat soft. This observation may be explained by the much lower glass transition temperature of PLA (60° C.) as compared to ABS (105° C.); the friction generated by twisting a pedicle-finding probe or inserting a pedicle screw into the PLA model likely causes the model to deform locally rather than break. On the other hand, ABS would readily break when contacting a twisting pedicle probe, creating a feeling very similar to that of human bone. Given that the ABS and PLA models appeared to perform with equivalent reliability in terms of their linear associations between print variables and tested outcomes, it is believed that ABS is the most promising of these 3 materials tested for further development and use as a synthetic model of a lumbar vertebra.

Also significantly impacting the tested outcomes were in-fill pattern and print orientation. Interestingly, in-fill pattern predictably impacted all 3 tested outcomes, with the diamond pattern producing higher IT, APO, and ST values than the hexagonal and linear patterns. This finding will be important when selecting specific print parameters for the creation of synthetic vertebral body models that will be instrumented, as the choice of in-fill pattern will significantly impact the screw performance in those models. Similarly, the print orientation had a highly significant impact on the tested outcomes, although the direction of effect was different for IT than for APO and ST. This finding likely relates to the observation that the models tended to fail on APO testing in a plane parallel to the print orientation. The IT was measured during screw insertion, whereas the APO and ST were measured during screw pullout. The impact of the print orientation is therefore likely to impact the tested outcomes differently during these tests.

For the ABS models, in-fill had a significant effect on IT and APO but not on ST. Similarly, in-fill pattern significantly affected IT and APO but not ST. However, ST was significantly different among vertebral body models of different material. Perhaps this finding indicates that ST is more affected by material type than the other tested outcomes.

Comparison to Historical Data

By using the linear regression analysis correlating APO and BMD that was published, BMD likely to mimic can be predicted with certain model materials and print settings. Nylon, for example, had a mean (SD) APO force of 223 (103) N; using the Halvorson et al. linear regression, this value correlates with a BMD<0.6 g/cm$^2$. A BMD value this low represents extreme osteoporosis and falls off the normal curve entirely. On the other hand, the mean APO force for ABS (1104 N) and PLA (2713 [684] N) models would correlate with a BMD of approximately 1.0 g/cm$^2$ and >1.4 g/cm$^2$, respectively. The same type of comparisons to historic data can be performed for IT and ST. Previous studies correlating BMD with IT and ST show that the studied synthetic model produces IT and ST values similar to those described in these historical data and that these variables can be reliably predicted through changes in the model material, in-fill density, and in-fill pattern.[11-14] Thus, it is easy to imagine the studied synthetic models being printed to perform analogously on IT, APO, and ST to human bone of a specific BMD. These models have potential, therefore, to become promising new platforms for spine biomechanics research. Furthermore, this study validates their continued use as synthetic bone in our continued efforts to 3D print a synthetic spine model with high anatomical, radiographic, and biomechanical fidelity to human tissue.

Future Considerations

Since the present study was conducted, a synthetic vertebral body model was developed that includes a standard pedicle trajectory printed into it. Similar testing is planned to test IT, APO, and ST in this model to determine whether this modification decreases the variability of results among models.

Testing of spinal segment range of motion has also been conducted in a similar fashion to determine the best print parameters of soft tissue components to achieve a synthetic spine model that mimics the human spine in range of motion and compression testing.

Testing Conclusions

The 3D-printed vertebral body models made of ABS and PLA performed analogously to human bone on pedicle screw tests of IT, APO, and ST. By altering the material, in-fill density, in-fill pattern, and print orientation of the synthetic vertebral body models, one could reliably produce a model that mimics bone with a specific BMD. As such, these synthetic models represent a promising new tool in spine biomechanics research, and they have promising potential utility in the fields of surgical planning and surgical education.

Additional Synthetic Components and Other Embodiments

Figure 18:
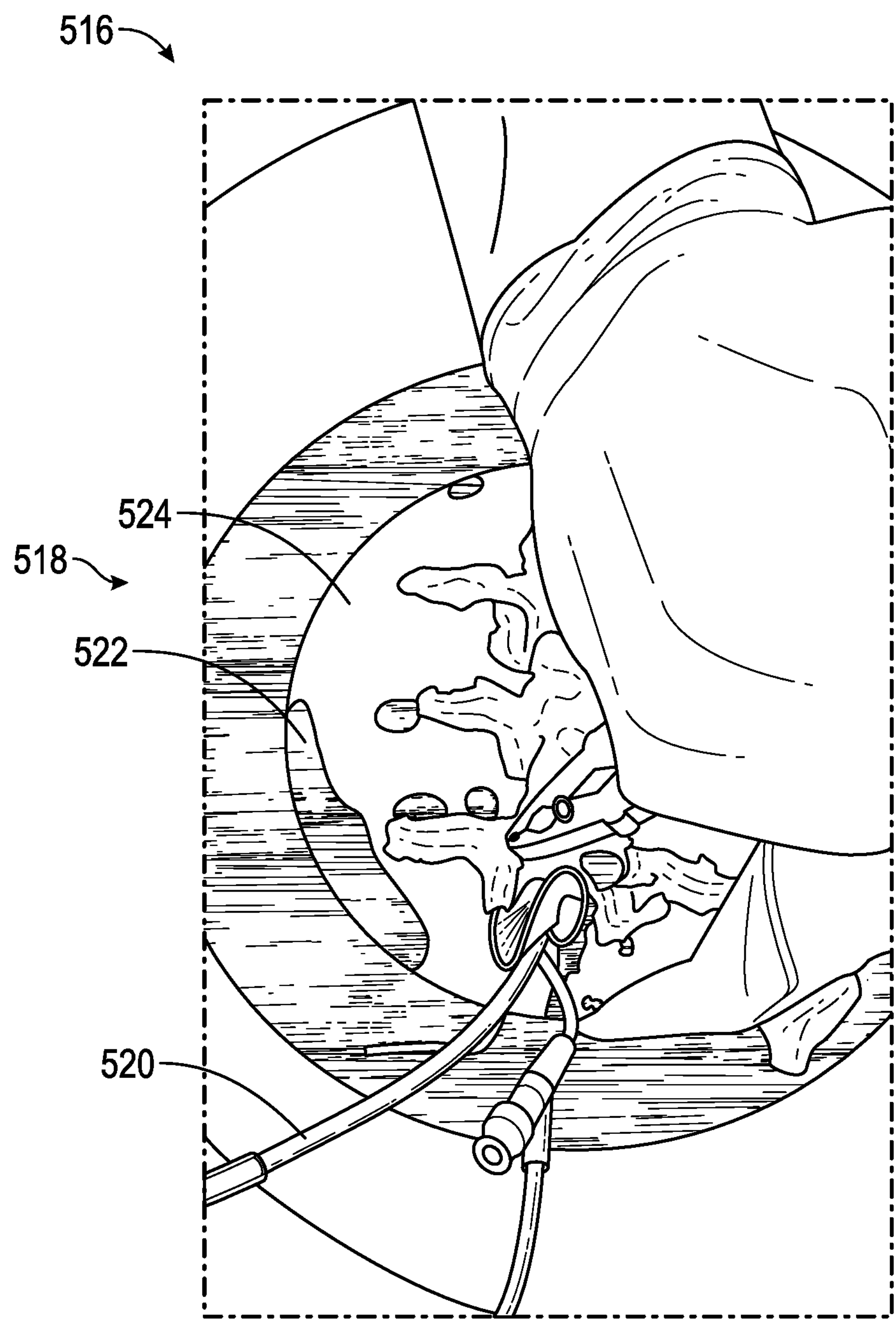
FIG. 18 is an image demonstrating artificial bleeding of synthetic bone.

Many additional synthetic anatomical components and additional embodiments and features are contemplated in view of the above description. For example, in one non-limiting embodiment, the synthetic anatomical model 116 may comprise a plurality of connecting ports disposed between adjacent vertebral segments and positioned on the interior surface of the vertebral segments, on the exterior surface of the vertebral segments, or a combination of both. At least one of these connecting ports may be configured to accommodate and releasably engage surgical tubing to one or more vertebral segments by any mechanism or structure or by any method or process suitable for, and capable of, maintaining or securing the surgical tubing in the desired position. For example, the synthetic anatomical model 116 may be printed with a plurality of connecting ports that can receive the surgical tubing which and held in a coaxial position by an adhesive or by predetermining the position of the plurality of connecting ports and the surgical tubing and configuring the diameter of the plurality of connecting ports in such a manner that the fitting between the plurality of connecting ports and surgical tubing restrains the surgical tubing from unwanted movement. It should be considered that surgical tubing is intended to read as any substantially flexible or rigid tubing suitable for transferring liquids, gases, semi dissolved solids, or any combination of these, used in the medical field. In this embodiment, the plurality of connecting ports and the surgical tubing may be adapted or designed to contain and carry any material, liquid, or substance capable of forming artificial blood. For example, FIG. 18 illustrates an exemplary printed anatomical model 516 outfitted with such connecting ports 518 and surgical tubing 520 integrated to the printed anatomical model 516 to simulate bleeding bone. In FIG. 18, the depicted bone is being bitten with a rongeur, and artificial blood 522 is seen spilling from the printed anatomical model 516 (through a connecting port, not shown). In this example, in one non-limiting embodiment, the artificial blood may be comprised of water or another similar aqueous solution and a red color additive (and possibly other ingredients) in order to closely replicate the consistency and aesthetics of a patient's blood.

As indicated in block 214 of FIG. 2A, in some non-limiting embodiments, the testing procedures may include drilling into or through a portion of the synthetic anatomical model 116 in order to separate the lamina from the rest of the vertebral segment, or to create pilot holes for pedicle screw insertion. In this non-limiting embodiment, the vertebral segments of the synthetic anatomical model 116 may comprise the plurality of connecting ports 518 and the surgical tubing 520 which contains the artificial blood 522 and mimics cadaveric bleeding when punctured by the tester's surgical tool. Thus, the plurality of connecting ports 518 may simulate a synthetic or artificial circulatory system that hemorrhages similar to a natural circulatory system.

In another non-limiting embodiment, the surgical tubing 520 described may be connected to an external pump (not shown) and artificial blood source (not shown) such that the artificial blood may be pumped to, and through the external pump and then through the surgical tubing to emulate a patient's natural circulatory system. It is considered that the artificial blood source may be any container or receptacle configured for and capable of storing the artificial blood. This operation can further be controlled by a series of valves (not shown) configured to control the flow of the artificial blood through the tubing and synthetic anatomical model 116. These valves may be used to create pockets of pressurized areas within the synthetic anatomical model 116 to impede the flow of artificial blood to specific areas.

In yet another non-limiting embodiment, the synthetic anatomical model 116 may further include an artificial soft tissue layer, illustrated as soft tissue layer 524 of FIG. 18, overlaying the synthetic model such that the synthetic anatomical model 116 is completely or partially disposed within the artificial soft tissue layer 524. In this non-limiting embodiment, the artificial soft tissue layer 524 may include e.g., Styrofoam, or may be comprised out of any material or substance suitable for the tester's preference without departing from the scope of this disclosure. For example, it is considered that the soft tissue layer 524 may be comprised of some flexible or inflexible material such as a silicone, rubber, elastomeric polymer, foam, or combinations thereof. Moreover, the artificial soft tissue layer 524 may comprise multiple segments of varying thickness, density, and chemical properties. In essence, the artificial soft tissue layer 524 may function to provide not only the major structural and physical characteristics of human soft tissue, but any structure and physical characteristics of the human body that may be suitable for the testing procedure. Thus, dural layers, cartilage, bone, ligaments, ancillary tissue may all be formed as part of the soft tissue layer 524 of the high fidelity synthetic anatomical model 116.

Figure 19:
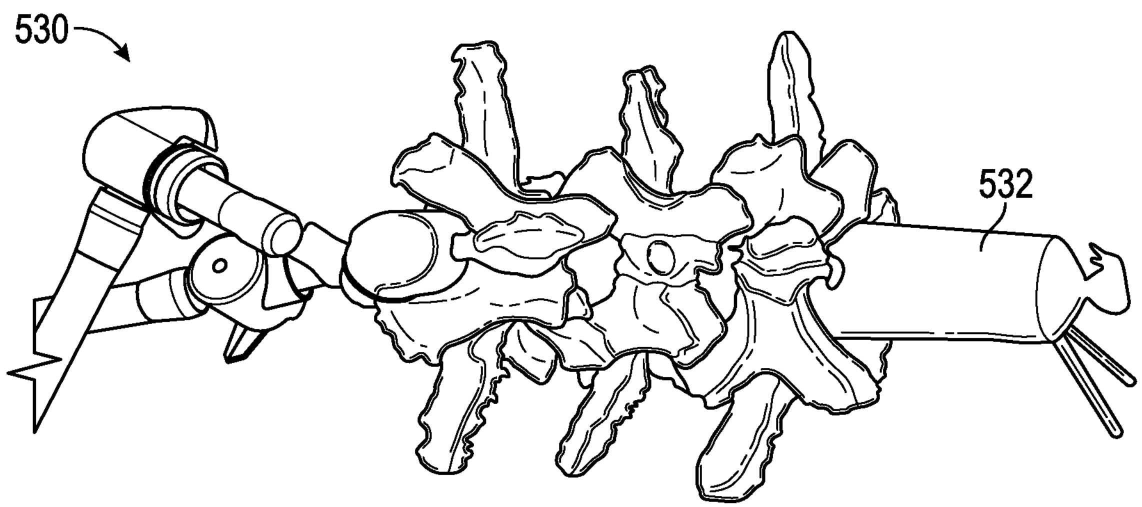
FIG. 19 is an image demonstrating a synthetic thecal sac.

In yet another non-limiting embodiment, the synthetic anatomical model 116 can be constructed with a synthetic thecal sac 532, as illustrated by a synthetic anatomical model 530 shown in FIG. 19, configured to have a tubular structure that reflects a patient's anatomical proportions and constructed out of any material or substance suitable for the testing procedure that mimic's a patient's thecal sac without departing from the scope of the disclosure. To illustrate, it is considered that the thecal sac 532 may be comprised out of any transparent or colored polymer, silicone, rubber, wax, resin, collagen, or any combinations thereof. Furthermore, the material may also be substantially impermeable to water or other liquid solutions in order to prevent unwanted permeation of the liquid solution throughout the synthetic anatomical model 116. In this arrangement, the thecal sac 532 may be completely or partially hollow to comprise an interior portion (not shown) such that the interior portion may be completely or partially filled with water or another liquid solution that mimics cerebrospinal fluid. When a non-limiting embodiment like this is adopted, the interior portion may have a pressurized environment such that liquid solution can mimic the cerebrospinal fluid inside a patient's thecal sac to a relatively high degree of fidelity. To illustrate, during the testing procedure the thecal sac 532 can be used for practicing surgical procedures such as a laminectomy. In this instance, if the underlying thecal sac is punctured during the test, internal pressure from the synthetic anatomical model 116 will force the liquid solution through the punctured portion of the model where it will be visible by the surgeon; the surgeon may then practice repairing the thecal sac 532 in accordance with general durotomy procedures. The thecal sac 532 can also contain certain materials that mimic the spinal cord and/or nerve roots, to increase the face validity of the synthetic model as a surgical training platform. In addition, the thecal sac 532 described may be configured to attach to the synthetic anatomical model 116 by any mechanism or structure or by any method or process suitable for, and capable of, maintaining or securing the thecal sac 532 in a desired position. For example, the synthetic thecal sac 532 and the synthetic anatomical model 116 may be each printed as a separate component and combined together using an adhesive agent or similar component. The thecal sac 532 can alternatively be constructed in a non-3D printing process and added to the synthetic anatomical model 116. In the specific example of FIG. 19, the thecal sac 532 is composed of synthetic collagen which is added to the synthetic anatomical model 530 after printing. The thecal sac 532 may be connected to a source of fluid that mimics cerebrospinal fluid, so that when the thecal sac 532 is injured (e.g., penetrated or ruptured), the thecal sac 532 may leak fluid under pressure to mimic operative conditions.

In yet another non-limiting embodiment, the thecal sac 532 described may also comprise at least one pressure sensor (not shown) that detects signals from an external force applying pressure and transmits that signal to a receiver (not shown). The specific signal transmitting methods may comprise any communications link, method, or process suitable for detecting the external signal, including a transmitter, transceiver, controller, processor receiver and a means for displaying the external signal to the surgeon as well as a power source (not shown) that is configured to be coupled with the at least one pressure sensor and may supply the at least one pressure sensor with sufficient power to maintain operation. To illustrate this non-limiting embodiment, the external signal may be displayed to the surgeon through an external display screen (not shown) of a personal computer. In the event that there is more than one pressure sensor, each sensor may have a different position and orientation within the synthetic anatomical model 116 that may be useful for the specific testing procedure. For instance, the sensor or a network of sensors may be placed within the thecal sac 532 at various locations to correspond with the relative position of the vertebral segments that are to be removed by the surgeon. In accordance with this non-limiting embodiment, the training procedure may require accurate tracking of the surgeon's movements to avoid real life instances of a durotomy caused by the surgeon's tool piercing the thecal sac 532 and/or the underlying layers. As such, the sensor may be integrated into the synthetic anatomical model 116 to provide the surgeon with an accurate measurement of the position of the surgeon's tool within the synthetic anatomical model 116 which may then be transferred through a communications link to a display (not shown). In this case, the tool may be any type of medical tool suitable for this procedure, such as a high-speed drill, scalpel, etc. The at least one sensor may be calibrated to the surgeon's preference prior to or during the testing procedure.

In yet another non-limiting embodiment, the pressure sensor may be configured to directly elicit an auditory or visual signal when activated so that it provides the surgeon with real-time feedback on the location of the surgeon's tool within the synthetic anatomical model 116. For example, at least one pressure sensor may be positioned directly beneath the lamina and on the dural layer of the synthetic anatomical model 116 such that when the surgeon's tool strikes the sensor, it will immediately elicit an auditory signal alerting the surgeon to the position of their surgical tool. In still other non-limiting embodiments, the at least one pressure sensor may be configured to couple with at least one optical component (not shown) integrated into the synthetic anatomical model 116 and positioned along or in the device in any method that is suitable for the testing procedure and to the user's preference. In this non-limiting embodiment, when the at least one pressure sensor is activated, it will send a signal to the optical component which elicits an illuminatory response, allowing the surgeon to observe the signal response in real-time. For example, in this non-limiting embodiment, the synthetic anatomical model 116 may have an LED or series of LEDs (not shown) embedded within the device, but within the surgeon's view, such that when the surgeon's tool strikes the pressure sensor (not shown), the LED is illuminated and allows the surgeon to correct their technique.

Figure 20:
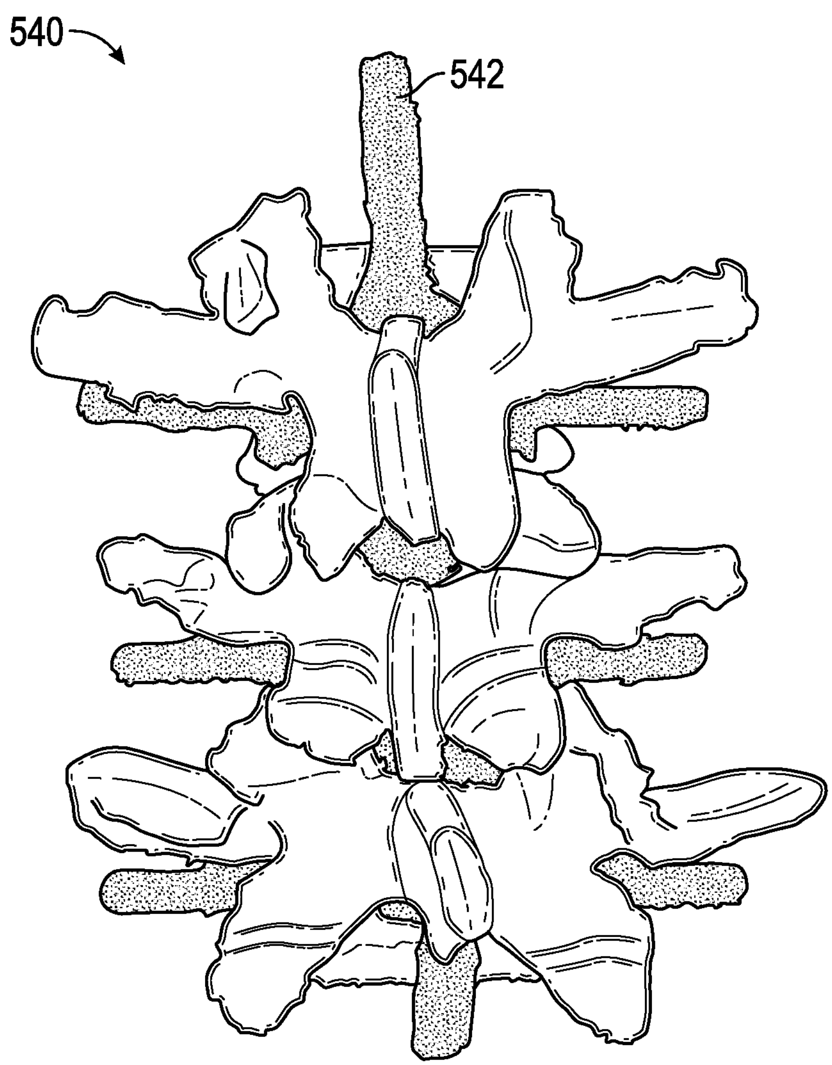
FIG. 20 is an image demonstrating printed conductive 3D synthetic neural elements or nerve roots.
Figure 21:
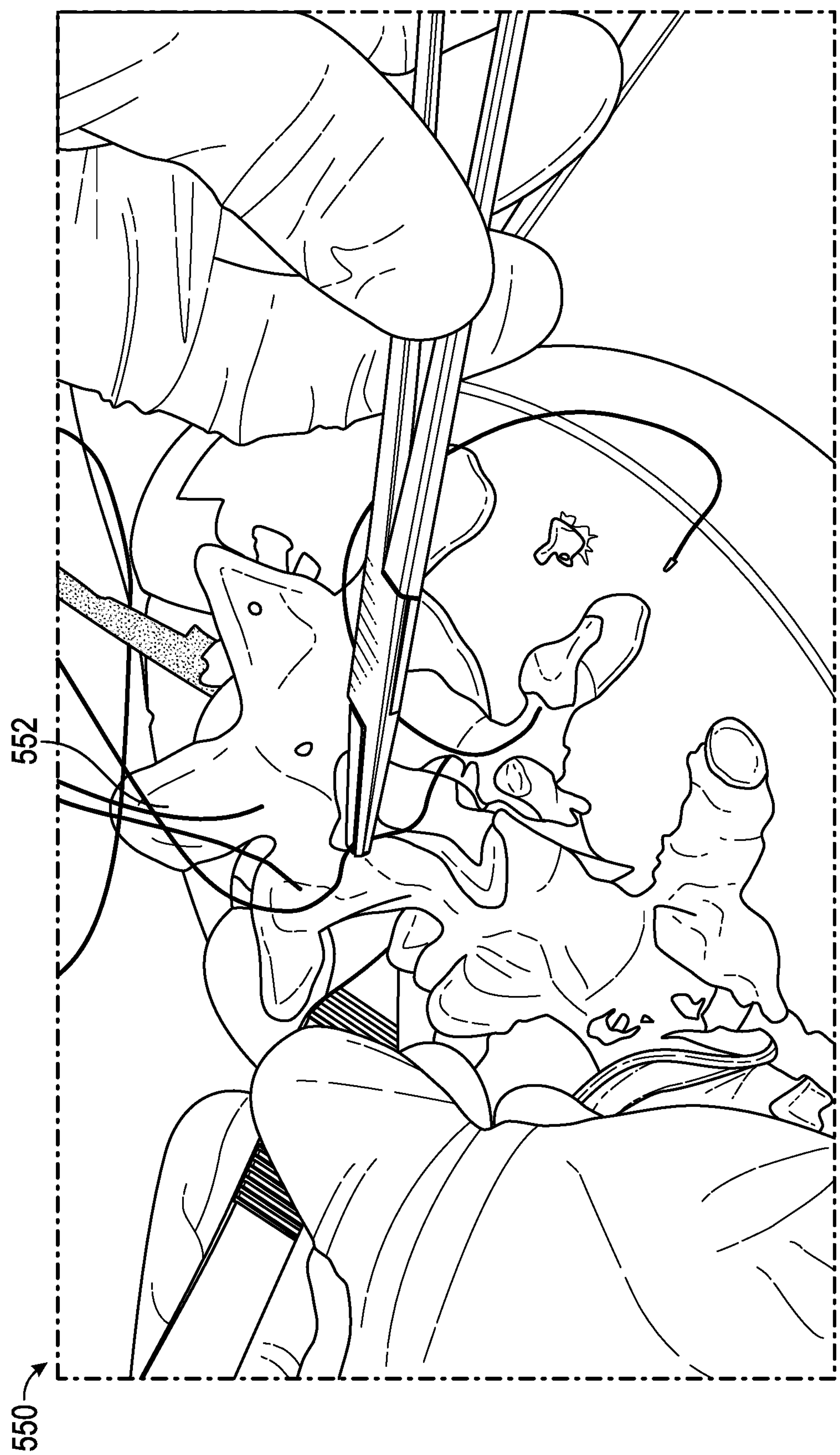
FIG. 21 is an image demonstrating conductive synthetic nerve roots added to a model after printing.
Figure 22:
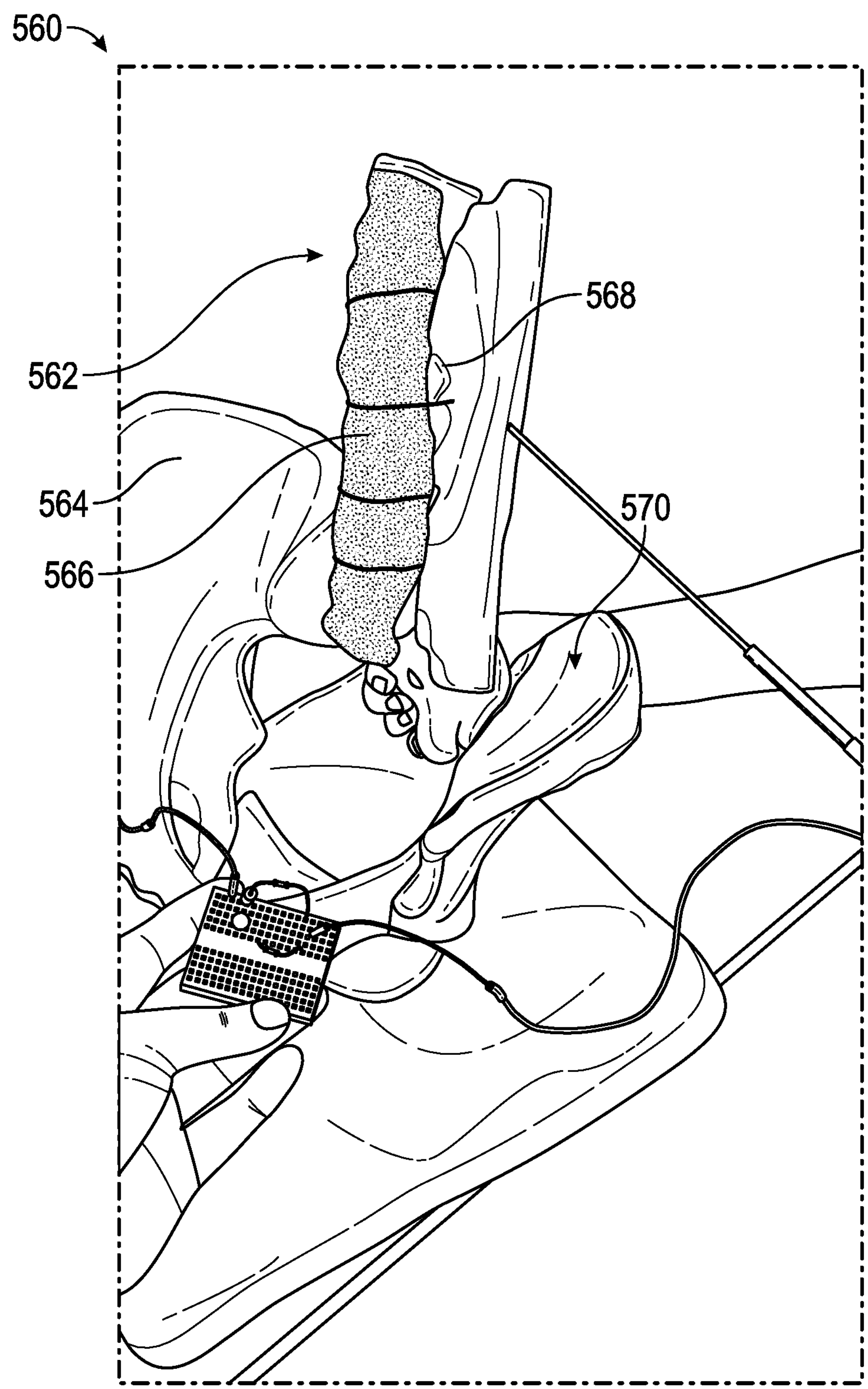
FIG. 22 is an image demonstrating synthetic 3D printed psoas muscle with nerve roots running through it.

In another embodiment, the synthetic anatomical model 116 may be constructed with neural elements and/or conductive nerve roots. FIG. 20, for example, illustrates a synthetic anatomical model 540 of L3-L5 segments with synthetic neural elements 542 formed using a thermoplastic mixed with graphite that enables it to conduct electricity after being 3D printed. FIG. 21 illustrates a synthetic anatomical model 550 with synthetic conductive nerve roots 552 formed using leads or conductive wires/layers configured to conduct electricity through or around the synthetic anatomical model 550 after the synthetic anatomical model 550 has been printed. FIG. 22 illustrates a synthetic anatomical model 560 of an L1-pelvis with electrically conductive neural elements 562 in the form of copper wire (but may also be embodied with other conductive materials). In this embodiment, the synthetic anatomical model 560 includes 3D printed bone 564, 3D printed anterior longitudinal ligament and intervertebral discs 566, and psoas muscle 568. The electrically conductive neural elements 562 run from the spinal canal 570 through the psoas muscle 568 in the same trajectory as anatomically seen in humans. In this example, a surgeon may apply an electrical stimulus with a metal probe, and when the probe begins to approach one of the simulated electrically conductive neural elements 562, the surgeon may be alerted as to the presence of a nerve root (by an audio or visual stimulus). This enables simulation of operative conditions and provides the same physiological feedback that a living human spine would provide a surgeon.

Figure 23:
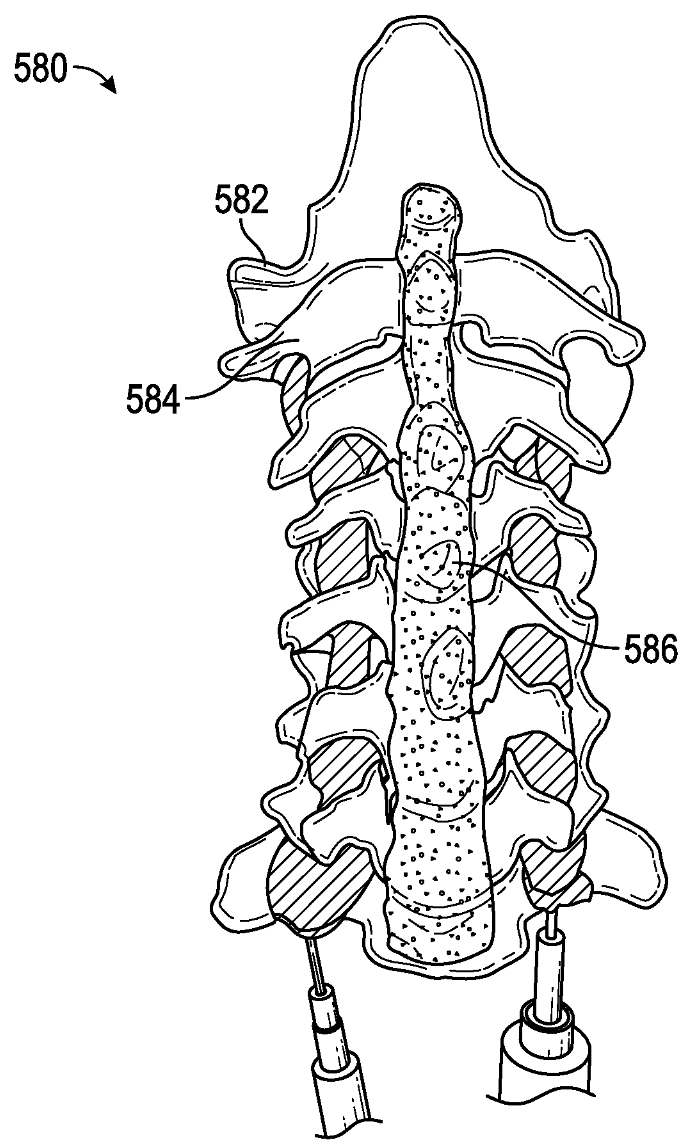
FIG. 23 is an image demonstrating arterial blood vessels added to a synthetic anatomical model.

In another non-limiting embodiment illustrated by the synthetic anatomical model 580 of a cervical spine shown in FIG. 23, the synthetic anatomical model 116 may be formed with vertebral arteries 582 that bleed if injured or ruptured. In this example, the synthetic anatomical model 580 further includes 3D printed synthetic bone 584, and synthetic ligamentous structures 586. The vertebral arteries 582 may be formed using collagen sacs, and may also incorporate aspects of FIG. 18 including the plurality of connecting ports 518 and the surgical tubing 520 used to distribute artificial blood through the model.

Figure 24:
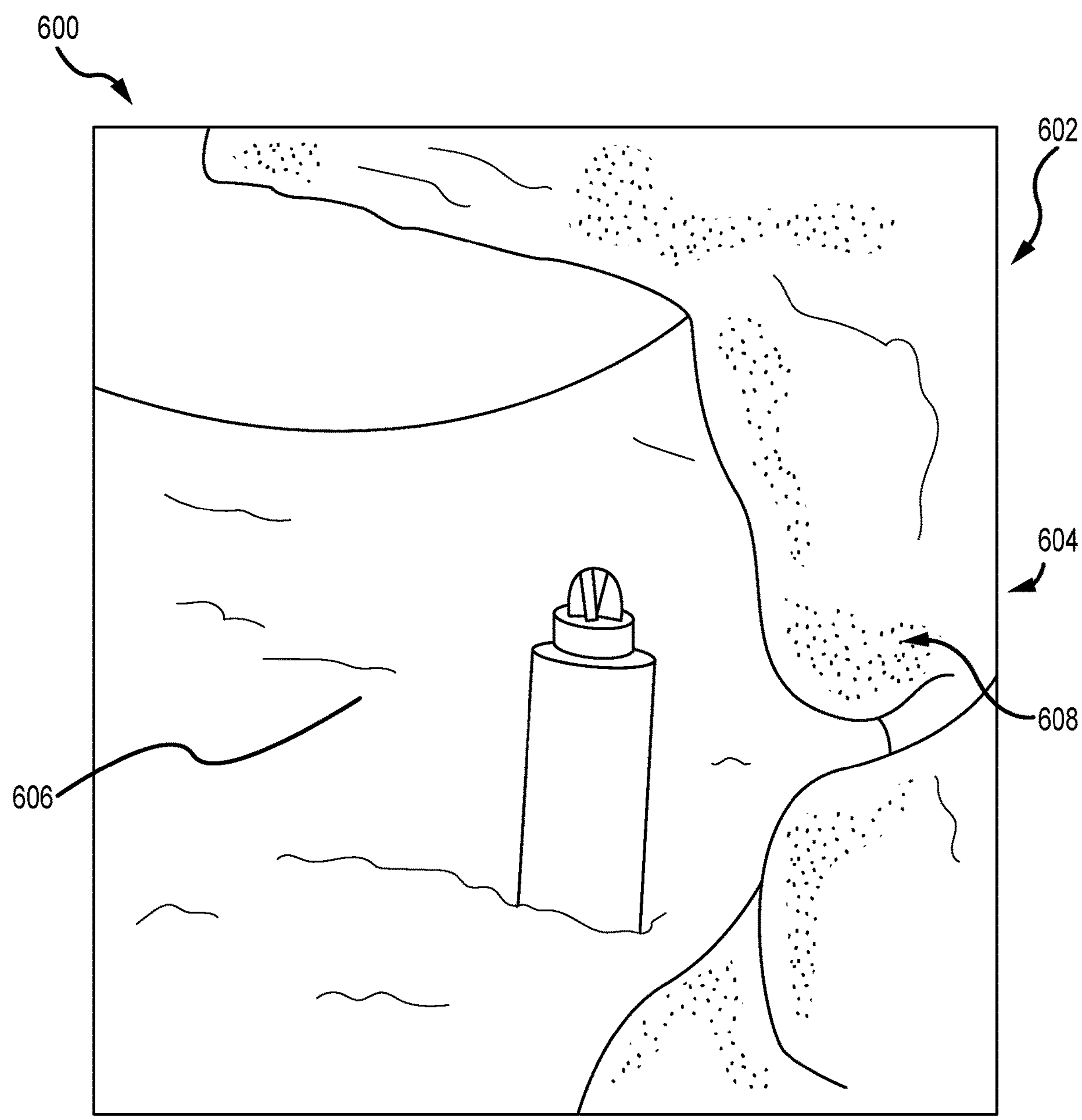
FIG. 24 is a microscopic surgical view of an image demonstrating radiolucent soft tissue deployed with an anatomical model.

In another non-limiting embodiment illustrated by the synthetic anatomical model 600 of a cervical spine shown in FIG. 24, radiolucent soft tissue made of foam may be formed along the synthetic anatomical model 116. In this example, the synthetic anatomical model 600 also includes 3D printed synthetic bone 604, synthetic ligamentous structures 606, and a synthetic thecal sac 608.

Figures 25, 26:
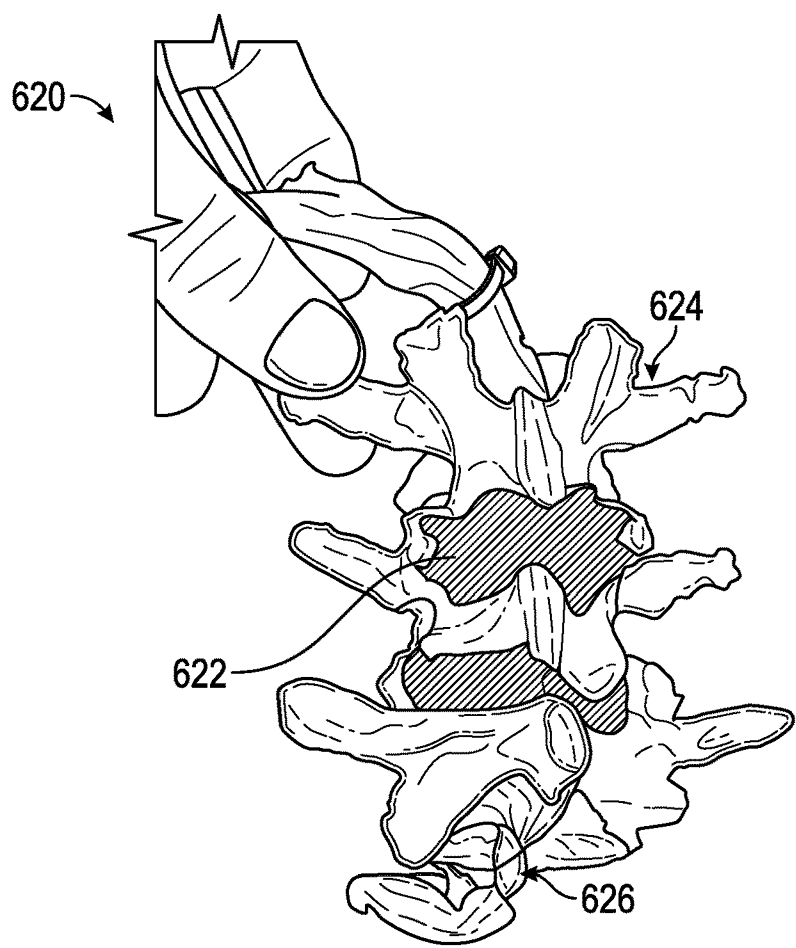
FIG. 25 is an image demonstrating synthetic ligamentum flavum integrated into a model.
FIG. 26 is an image demonstrating a synthetic spinal segment with synthetic collagen simulating a periosteum tissue layer covering the bone.

In another non-limiting embodiment illustrated by the synthetic anatomical model 620 (L3-L5 spinal model) of FIG. 25, the synthetic anatomical model 116 may further be constructed with a synthetic ligamentum flavum 622 oriented in the interlaminar space which may be formed after 3D printing of synthetic bone material 624 shown. FIG. 25 further shows another example of a synthetic thecal sac 626.

In another non-limiting embodiment illustrated by the synthetic anatomical model 640 (L3-L5 spinal model) of FIG. 26, the synthetic anatomical model 116 may further be constructed with a synthetic periosteum tissue layer 642 positioned over the spinous processes of L3 and L4 which may be formed or added after 3D printing of synthetic bone material 644 as shown. The synthetic periosteum tissue layer 642 may be formed using collagen or other similar material and may be added after 3D printing of the synthetic bone material 644. In another non-limiting embodiment, the synthetic anatomical model 116 or any of the synthetic anatomical components described may be directly implanted within a subject, or use for testing. It is also contemplated that the component may be printed directly into the subject's anatomy without departing from the scope of the disclosure. It is also contemplated that the printed or artificial anatomical components of the present inventive concept are capable of biodegradation, bioabsorbtion, or both, whether it is being used as a temporary implant, or for another purpose suitable for the user's needs. To illustrate, it is contemplated that the synthetic anatomical model 116 may be constructed out of a degradable or absorbable material such that it may act as a temporary support structure in the subject's body, thereby improving biomechanical stability of other constructs. Indeed, the synthetic anatomical model 116 could be printed to include or carry biological agents such as bone graft extenders, bone morphogenic proteins, or other suitable agents.

Figure 28A:
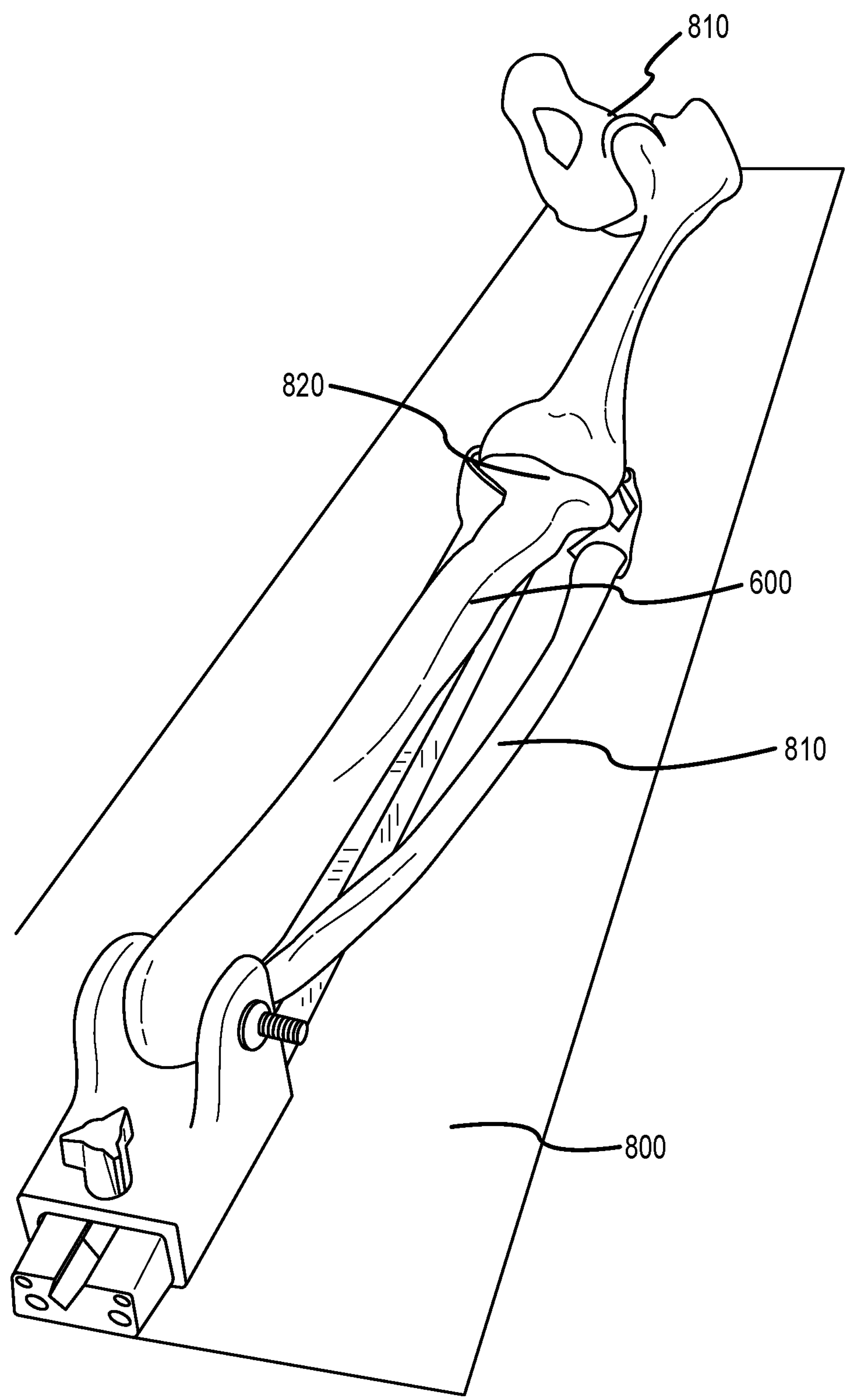
FIG. 28A is an image of a base constructed to support and guide movement of a synthetic anatomical model where the model is in an extended position.
Figure 28B:
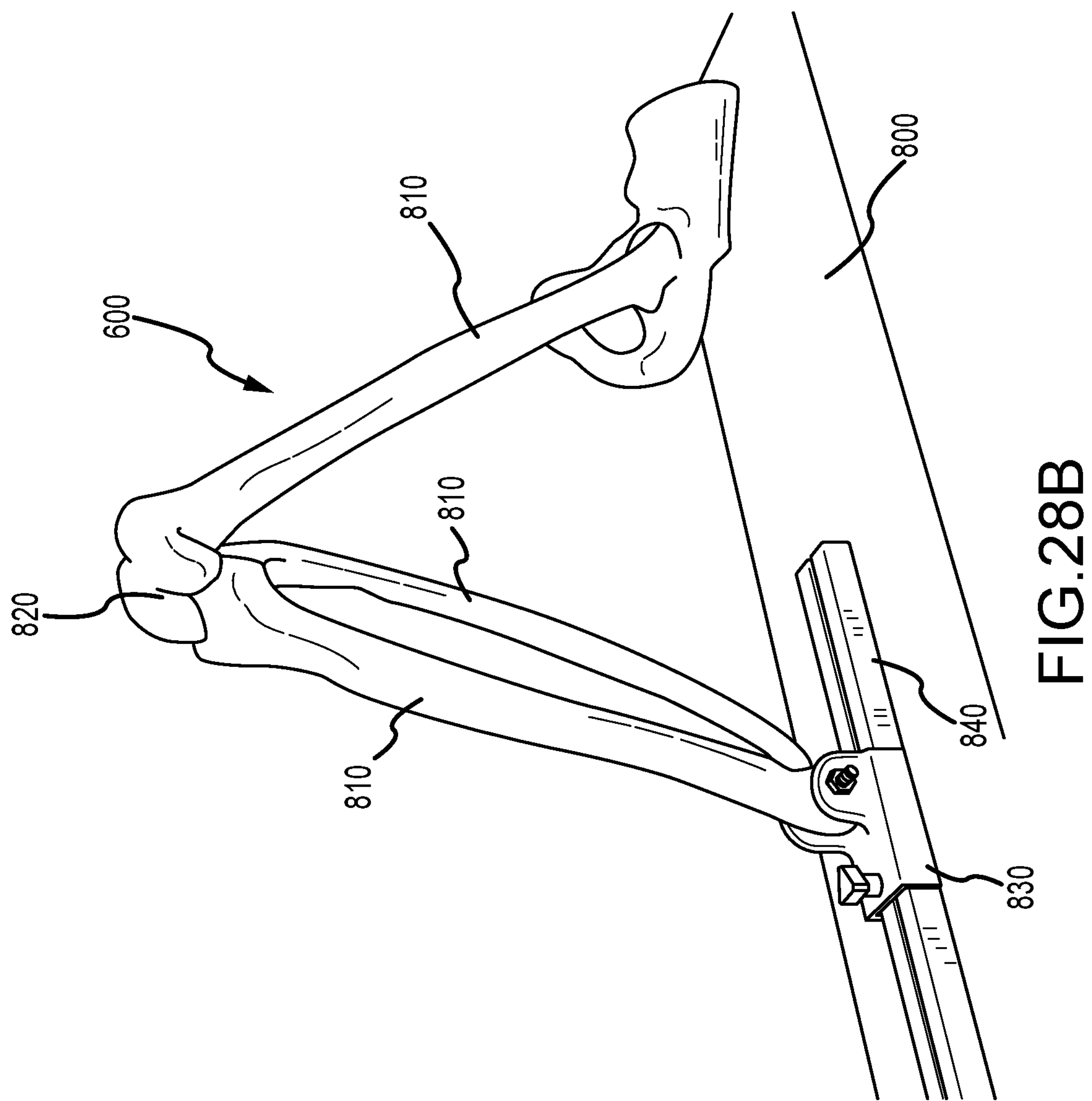
FIG. 28B is an image of a base constructed to support and guide movement of a synthetic anatomical model where the model is in a flexed position.

In another non-limiting embodiment illustrated in part by the synthetic anatomical model of a knee in FIGS. 28A-B, a base 800 or frame may be constructed to hold or otherwise support the synthetic anatomical model. The base 800 is constructed to securely hold the synthetic anatomical model 600 and/or guide movement of the synthetic anatomical model in a range of motion that is biomechanically tested and reflects the range of motion of human subjects. The base may be formed using a polymeric resin or other materials such as wood, metals, and composites and the like. The base may include moving rail systems to facilitate natural movement and locking mechanisms to hold the synthetic anatomical model in a specific orientation with a goal of stabilizing the synthetic anatomical model for surgical instrumentation or inspection. For example, FIG. 28A illustrates synthetic anatomical model 600 in the form of leg bones 810 and a knee 820 in an extended position, while FIG. 28B illustrates synthetic anatomical model 600 after moving one end of the leg bones 810 which has been connected to hinged slide assembly 830 that can slide along a track 840 to a flexed position. In alternative configurations, bases and frames for other synthetic anatomical models of other physical anatomy may be constructed to hold or otherwise support that particular synthetic anatomical model and to guide the movement of that particular anatomy.

In some embodiments, different configurations of 3D printer filament materials and printing parameters (based on the experimentally derived datasets 112) may be used to print different types of human tissue in the spinal column (including, but not limited to, cortical bone, medullary bone, annulus fibrosus, nucleus pulposus, anterior longitudinal ligament, posterior longitudinal ligament, ligamentum flavum, interspinous ligament, supraspinous ligament, facet joint and capsule, blood vessels, spinal cord and nerve roots, dura, and muscle/muscle attachments). These materials may be printed either directly into each other, printed individually and later assembled, or constructed separately through a combination of additive manufacturing and other manufacturing processes (i.e. silicone rubber or foam pouring) and then later added together.

Figure 29A:
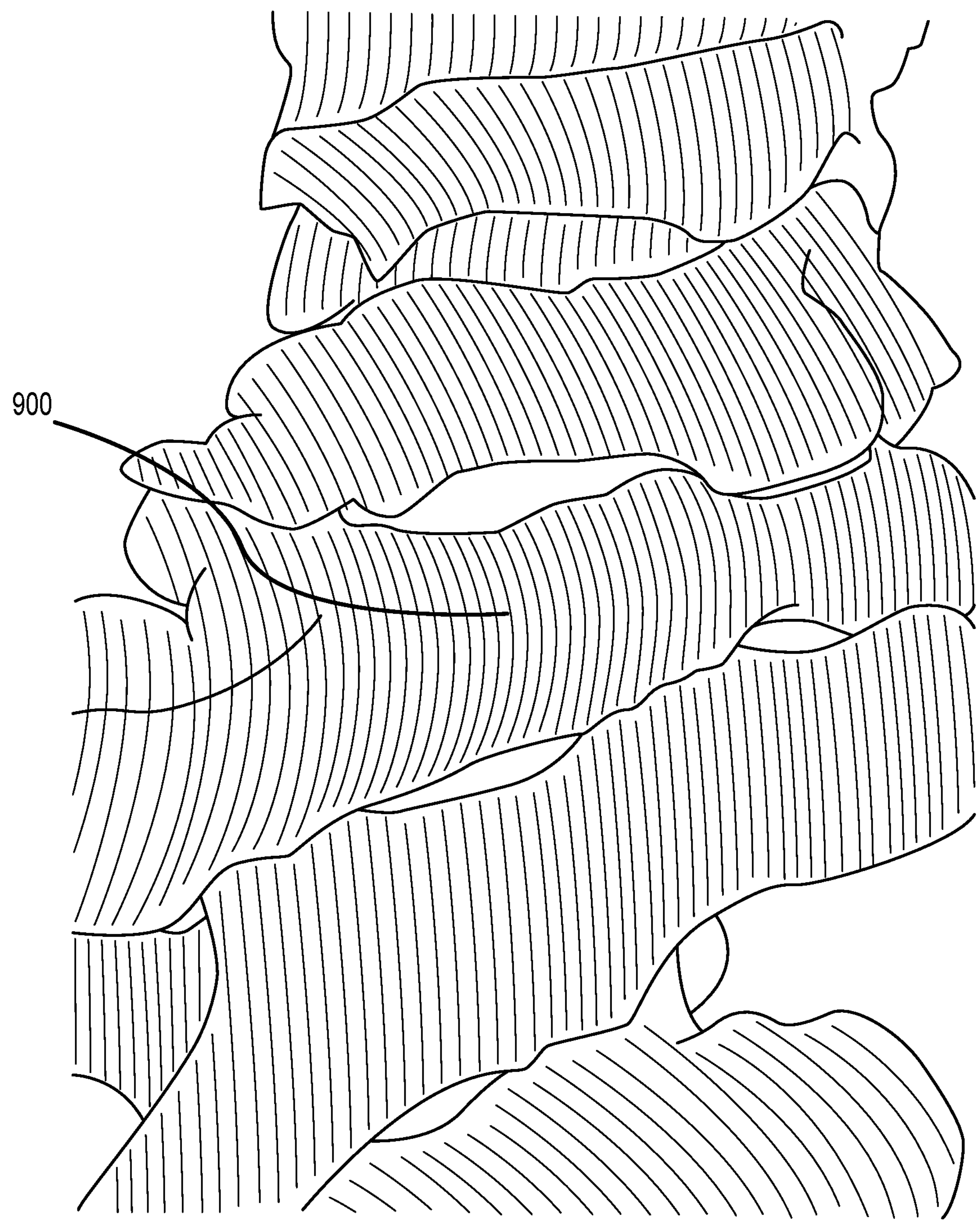
FIG. 29A is an image demonstrating distinct and less fused layers of a 3D printed synthetic spinal segment.

In some embodiments, one or more portions of the synthetic anatomical model may further include a coating that enhances the model's biomechanical, fluoroscopic, and surgical handling characteristics. For example, synthetic anatomical models created using filament deposition modeling technologies can be prone to cracking and splitting along layers of 3D printed material. This splitting negatively impacts the biomechanical and surgical handling performance of the synthetic anatomical model. For example, FIG. 29A illustrates distinct layers 900 post-printing, prior to application of a coating, which may be prone to splitting.

Figure 29B:
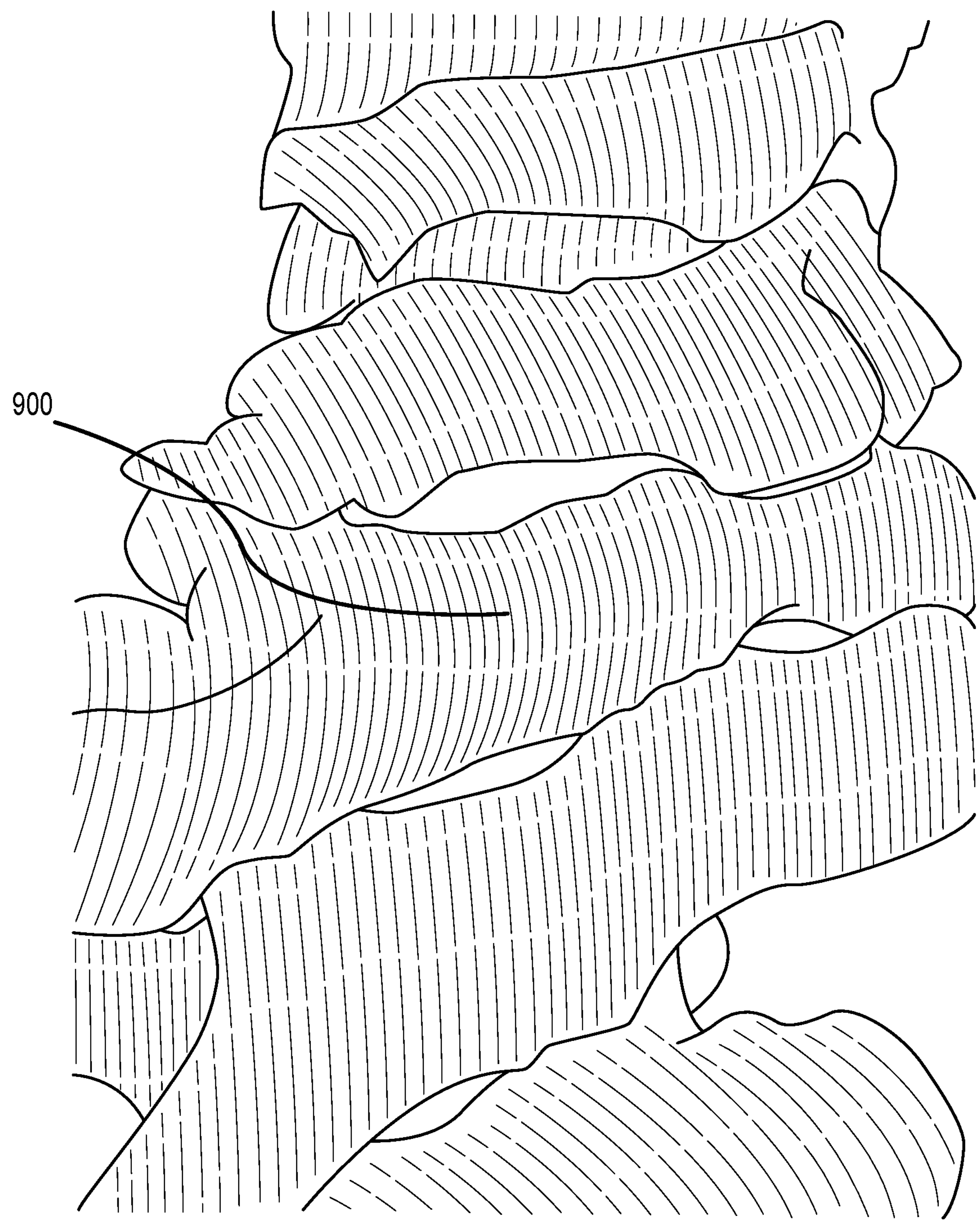
FIG. 29B is an image demonstrating less distinct layers in a 3D printed synthetic spinal segment that are fused together by application of a solvent.

By treating the synthetic anatomical model with a solvent after printing, either by direct application of a liquid solvent or exposure of the synthetic anatomical model to an aerosolized or gaseous form of the solvent, the external layers of the synthetic anatomical model are essentially "melted" and better fused together. As seen in FIG. 29B, after application of the coating, the layers 900 are less distinct and more strongly fused together. Such treatment of the synthetic anatomical model with a solvent in this fashion helps prevent model splitting and cracking and improves both biomechanical performance and surgical handling of the synthetic anatomical model. Coatings can also include, but are not limited to, paints, adhesives, and sprays. Certain coatings can also be applied to improve the fluoroscopic performance of the synthetic anatomical model. For example, coating the bony components of the synthetic anatomical model with a zinc-containing paint will improve the fluoroscopic appearance of the bony components of the synthetic anatomical model. Examples of solvents that may be applied to the synthetic anatomical include 3D Gloop!, acetone (vapor or liquid) and the like.

In some embodiments, aspects of the synthetic anatomical model 116 may be printed with bony elements that are 3D printed using materials that are similarly radio-opaque to bone such that fluoroscopic and X-ray images can be taken of the model in a similar fashion to cadaveric specimens or living patients with similar results.

In some embodiments, utilizing functionality described herein, the synthetic anatomical components may include soft tissue elements such as annulus fibrosus, nucleus pulposus, anterior longitudinal ligament, posterior longitudinal ligament, ligamentum flavum, interspinous ligament, supraspinous ligament, facet joint and capsule, blood vessels, spinal cord and nerve roots, dura, and muscle attachments) that may be 3D printed according to the experimentally derived datasets 112 and configured print parameters (including, but not limited to, print shells, in-fill percentage, filament material, extruder temperature, print orientation, and in-fill pattern) to biomechanically perform in a predictable and reliable fashion that closely approximates a predetermined healthy or diseased state.

In some embodiments, the synthetic spine model 116 may be constructed with soft tissue elements (including, but not limited to, annulus fibrosus, nucleus pulposus, anterior longitudinal ligament, posterior longitudinal ligament, ligamentum flavum, interspinous ligament, supraspinous ligament, facet joint and capsule, blood vessels, spinal cord and nerve roots, dura, and muscle attachments) that are 3D printed using a material that is similarly radio-opaque to human soft tissue such fluoroscopic and X-ray images can be taken of the model in a similar fashion to cadaveric specimens or living patients with similar results.

The synthetic spine model 116 and other synthetic components described herein may be useful for many different applications. For example, the synthetic spine model 116 may reduce the variability of biomechanical testing results when using the method of FIG. 2A, as the model and each subsequently constructed model may be nearly identical to others created to the same parameters, thereby reducing the variability between models which is so common in cadaveric testing. The synthetic spine model 116 and other synthetic components may further be useful as a surgical skills training modality for spine surgeons and other trainees. There is a national push for the development of synthetic training models in specialized surgical fields, including spine surgery. For such models to have worthwhile utility as a training tool, they must possess high anatomical and biomechanical fidelity to living patients. The present method is capable of producing a synthetic spine model specific to any given patient's anatomy, with a biomechanical performance that can be customized to cadaveric disease states. As another example, the synthetic spine model 116 and other synthetic components may be useful as part of a testing platform for spinal instrumentation. Commercially available technology and the prior art currently lacks a synthetic spine model that permits testing of spinal instrumentation in an anatomically and biomechanically fidelic model that can be customized to various healthy and diseased spine states. The present method could also be used to create a model for use as a surgical planning tool for surgeons, as custom models of individual patients' spines could be created and then operated on prior to the patient's actual surgery.

Figure 27:
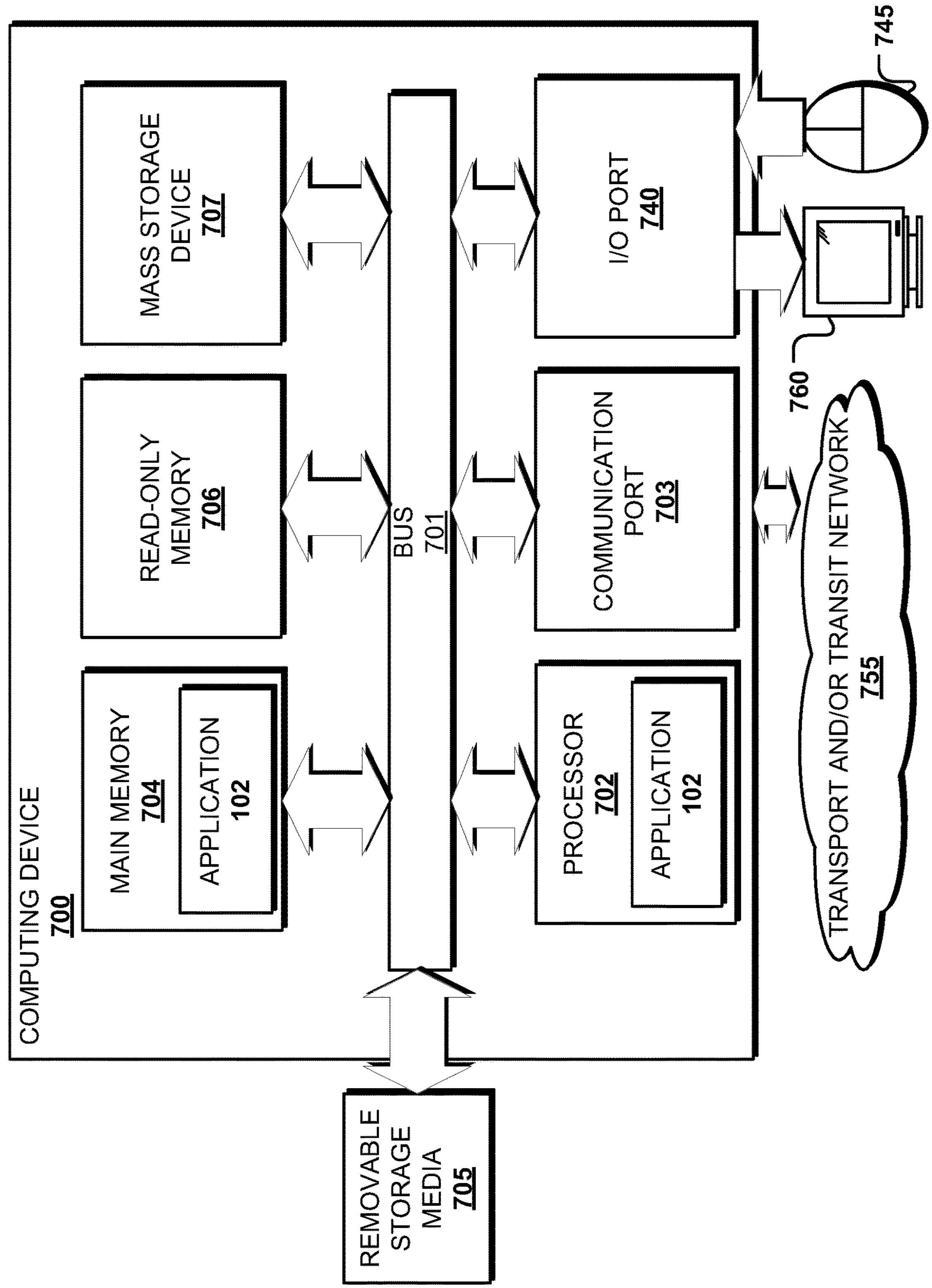
FIG. 27 is a simplified block diagram illustrating an example of a computing system that may implement various services, systems, and methods discussed herein.

FIG. 27 is an example schematic diagram of a computing device 700 that may implement various methodologies discussed herein. For example, the computing device 700 may comprise the computing device 104 executing or accessing functionality and/or aspects of the application 102. The computing device 700 includes a bus 701 (i.e., interconnect), at least one processor 702 or other computing element, at least one communication port 703, a main memory 704, a removable storage media 705, a read-only memory 706, and a mass storage device 707. Processor(s) 702 can be any known processor, such as, but not limited to, an Intel® Itanium® or Itanium 2® processor(s), AMD® Opteron® or Athlon MP® processor(s), or Motorola® lines of processors. Communication port 703 can be any of an RS-232 port for use with a modem based dial-up connection, a 10/100 Ethernet port, a Gigabit port using copper or fiber, or a USB port. Communication port(s) 703 may be chosen depending on a network such as a Local Area Network (LAN), a Wide Area Network (WAN), or any network to which the computer device 700 connects. Computing device may further include a transport and/or transit network 755, a display screen 760, an I/O port 740, and an input device 745 such as a mouse or keyboard.

Main memory 704 can be Random Access Memory (RAM) or any other dynamic storage device(s) commonly known in the art. Read-only memory 706 can be any static storage device(s) such as Programmable Read-Only Memory (PROM) chips for storing static information such as instructions for processor 702. Mass storage device 707 can be used to store information and instructions. For example, hard disks such as the Adaptec® family of Small Computer Serial Interface (SCSI) drives, an optical disc, an array of disks such as Redundant Array of Independent Disks (RAID), such as the Adaptec® family of RAID drives, or any other mass storage devices, may be used.

Bus 701 communicatively couples processor(s) 702 with the other memory, storage, and communications blocks. Bus 701 can be a PCI/PCI-X, SCSI, or Universal Serial Bus (USB) based system bus (or other) depending on the storage devices used. Removable storage media 705 can be any kind of external hard drives, thumb drives, Compact Disc-Read Only Memory (CD-ROM), Compact Disc-Re-Writable (CD-RW), Digital Video Disk-Read Only Memory (DVD-ROM), etc.

Embodiments herein may be provided as a computer program product, which may include a machine-readable medium having stored thereon instructions which may be used to program a computer (or other electronic devices) to perform a process. The machine-readable medium may include, but is not limited to optical discs, CD-ROMs, magneto-optical disks, ROMs, RAMs, erasable programmable read-only memories (EPROMs), electrically erasable programmable read-only memories (EEPROMs), magnetic or optical cards, flash memory, or other type of media/machine-readable medium suitable for storing electronic instructions. Moreover, embodiments herein may also be downloaded as a computer program product, wherein the program may be transferred from a remote computer to a requesting computer by way of data signals embodied in a carrier wave or other propagation medium via a communication link (e.g., modem or network connection).

As shown, main memory 704 may be encoded with the application 102 that supports functionality discussed above. In other words, aspects of the application 102 (and/or other resources as described herein) can be embodied as software code such as data and/or logic instructions (e.g., code stored in the memory or on another computer readable medium such as a disk) that supports processing functionality according to different embodiments described herein. During operation of one embodiment, processor(s) 702 accesses main memory 704 via the use of bus 701 in order to launch, run, execute, interpret, or otherwise perform processes, such as through logic instructions, executing on the processor 702 and based on the application 102 stored in main memory or otherwise tangibly stored.

It should be understood from the foregoing that, while particular embodiments have been illustrated and described, various modifications can be made thereto without departing from the spirit and scope of the inventive concept as will be apparent to those skilled in the art. Such changes and modifications are within the scope and teachings of this inventive concept as defined in the claims appended hereto.

What is claimed is:

1. A method, comprising:

accessing imaging data associated with a reference anatomical component for modeling;

utilizing a computing device and 3D printer in operable communication with the computing device, configured for:

creating a 3D printing file from the imaging data, the 3D printing file defining parameters for printing a polymeric synthetic model of the reference anatomical component;

adjusting the parameters of the 3D printing file according to experimentally derived datasets associated with anatomical, physiological, and biomechanical properties specific to the reference anatomical component;

printing at least a portion of the polymeric synthetic model of the reference anatomical component using the parameters as adjusted; and coating a surface of the polymeric synthetic model with a solvent to enhance at least one of a biomechanical, fluoroscopic, and surgical handling characteristics of the polymeric synthetic model.

2. The method of claim 1, wherein the imaging data is generated from multiple reference anatomical components from more than one subject to created integrated imaging data.

3. The method of claim 1, further comprising applying at least one biomechanical test to the polymeric synthetic model.

4. The method of claim 3, further comprising re-adjusting the parameters of the 3D printing file based on results associated with the at least one biomechanical test applied to the polymeric synthetic model.

5. The method of claim 1, wherein the reference anatomical component is associated with a CT scan of a patient.

6. The method of claim 1, wherein the experimentally derived datasets are derived at least based on biomechanical testing of a pedicle screw relative to a spinal segment of a cadaver.

7. The method of claim 1, wherein the polymeric synthetic model is printed with a first portion corresponding to a first configuration of print parameters and materials and a second portion corresponding to a second configuration of print parameters and materials, the first portion and the second portion simulating different portions of natural anatomy.

8. The method of claim 1, further comprising embedding the polymeric synthetic model at least partially within a synthetic soft tissue.

9. The method of claim 1, further comprising positioning a synthetic thecal sac along the polymeric synthetic model.

10. The method of claim 1, wherein the polymeric synthetic model is printed with a portion simulating a nerve element, the portion including a metal such that the portion is electrically conductive.

11. The method of claim 1, further comprising positioning a plurality of conductive wires along the polymeric synthetic model to represent nerve roots.

12. The method of claim 1, further comprising:

forming a plurality of channels through the polymeric synthetic model;

disposing a surgical tubing through the plurality of channels; and disposing an artificial blood solution within the surgical tubing under a pressure.

13. The method of claim 1, wherein the imaging data is derived from a CAD software package, and the imaging data, and the computing device is configured to convert the imaging data to STL files.

14. The method of claim 1, further comprising modifying the 3D printing file to adjust one or more features for the polymeric synthetic model.

15. The method of claim 1, wherein the polymeric synthetic model is printed to mimic corticocancellous architecture of human bone, the polymeric synthetic model including a mesh portion filing an interior of the polymeric synthetic model and having a first thickness, and the polymeric synthetic model further having a cortical outer shell of a second thickness greater than the first thickness positioned around the mesh portion.

16. The method of claim 1, wherein the polymeric synthetic model is printed with radio-opaque materials such that the polymeric synthetic model is visible under fluoroscopic and X-ray devices.

17. The method of claim 1, further comprising simulating a spinal correction procedure by applying a spinal fixation construct to the polymeric synthetic model.

18. The method of claim 17, further comprising identifying failure points of the reference anatomical component based on the spinal correction procedure applied to the polymeric synthetic model.

* * * * *